United States Patent
Chong et al.

(10) Patent No.: US 9,545,477 B2
(45) Date of Patent: *Jan. 17, 2017

(54) ON-BODY INJECTOR AND METHOD OF USE

(71) Applicant: MEDTRONIC MINIMED, INC., Northridge, CA (US)

(72) Inventors: Colin A. Chong, Glendale, CA (US); Randal Schulhauser, Phoenix, AZ (US); Tyler S. Stevenson, Phoenix, AZ (US); Rafael Bikovsky, Oak Park, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,989

(22) Filed: Jan. 15, 2016

(65) Prior Publication Data

US 2016/0129203 A1    May 12, 2016

Related U.S. Application Data

(63) Continuation of application No. 14/613,605, filed on Feb. 4, 2015, now Pat. No. 9,265,884, which is a
(Continued)

(51) Int. Cl.
*A61M 5/32* (2006.01)
*A61M 5/142* (2006.01)
(Continued)

(52) U.S. Cl.
CPC ......... *A61M 5/14248* (2013.01); *A61M 5/145* (2013.01); *A61M 5/158* (2013.01);
(Continued)

(58) Field of Classification Search
CPC ............. A61M 5/14248; A61M 5/31511; A61M 5/172; A61M 5/3287; A61M 39/02; A61M 5/16813; A61M 5/16804; A61M 39/0247; A61M 5/145; A61M 5/158; A61M 5/484; A61M 2005/14252; A61M 2039/0205; A61M 2005/14
See application file for complete search history.

(56) References Cited

U.S. PATENT DOCUMENTS 4,755,173 A    7/1988  Konopka et al.
4,781,688 A    11/1988 Thoma et al.
(Continued)

FOREIGN PATENT DOCUMENTS

EP    1403519 A1    3/2004
WO    02068015 A2    9/2002
(Continued)

OTHER PUBLICATIONS

PCT International Search Report and Written Opinion for PCT/US2014/059864 dated Mar. 3, 2015.
(Continued)

*Primary Examiner* — Theodore Stigell
*Assistant Examiner* — Amber Stiles
(74) *Attorney, Agent, or Firm* — Medtronic Minimed, Inc.

(57) ABSTRACT

An on-body injector and method of use including an on-body injector for use with an injection device. The on-body injector includes a bolus reservoir; a bolus injection needle in fluid communication with the bolus reservoir, the bolus injection needle having a bolus injection needle tip aligned with the injection port, the bolus injection needle being slideably biased away from the injection port to define a gap between the bolus injection needle tip and the injection port; and a button operably connected to the bolus injection needle to slide the bolus injection needle along the injection axis. The button is operable to advance the bolus injection needle tip to close the gap and advance the bolus injection
(Continued)

needle tip into the injection port. The button is further operable to advance a plunger through the bolus reservoir to deliver a predetermined bolus volume to the patient through the injection flow path.

18 Claims, 39 Drawing Sheets

Related U.S. Application Data continuation of application No. 14/134,749, filed on Dec. 19, 2013, now Pat. No. 8,979,808, which is a continuation-in-part of application No. 14/052,929, filed on Oct. 14, 2013, now Pat. No. 9,265,881.

(51) Int. Cl.
*A61M 5/48* (2006.01)
*A61M 5/158* (2006.01)
*A61M 5/145* (2006.01)
*A61M 5/168* (2006.01)
*A61M 39/02* (2006.01)
*A61M 5/172* (2006.01)
*A61M 5/315* (2006.01)

(52) U.S. Cl.
CPC .... *A61M 5/16804* (2013.01); *A61M 5/16813* (2013.01); *A61M 5/172* (2013.01); *A61M 5/31511* (2013.01); *A61M 5/3287* (2013.01); *A61M 5/484* (2013.01); *A61M 39/02* (2013.01); *A61M 39/0247* (2013.01); *A61M 2005/14252* (2013.01); *A61M 2005/14506* (2013.01); *A61M 2005/1585* (2013.01); *A61M 2039/0205* (2013.01)

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,979,808 B1 * | 3/2015 | Chong .................. A61M 5/484 604/246 |
| 9,265,884 B2 * | 2/2016 | Chong .................. A61M 5/484 |
| 2007/0123819 A1 | 5/2007 | Mernoe et al. |
| 2007/0156103 A1 * | 7/2007 | Chatlynne ............. A61M 5/152 604/257 |
| 2007/0270748 A1 | 11/2007 | Dacquay et al. |
| 2009/0028824 A1 * | 1/2009 | Chiang ............. A61M 5/14248 424/85.7 |
| 2010/0160861 A1 | 6/2010 | Causey, III et al. |
| 2011/0009823 A1 | 1/2011 | Chong et al. |
| 2011/0144587 A1 | 6/2011 | Stone |

FOREIGN PATENT DOCUMENTS

| | | |
|---|---|---|
| WO | 02068015 A3 | 9/2002 |
| WO | 2004024211 A2 | 3/2004 |
| WO | 2004024211 A3 | 3/2004 |
| WO | 2006032692 A1 | 3/2006 |
| WO | 2006108809 A1 | 10/2006 |
| WO | 2007108987 A2 | 9/2007 |
| WO | 2007108987 A3 | 9/2007 |
| WO | 2011133823 A1 | 10/2011 |

OTHER PUBLICATIONS

PCT International Search Report and Written Opinion for PCT/US2014/069945 dated Mar. 6, 2015.
PCT International Search Report and Written Opinion for PCT/US2014/069957 dated Mar. 6, 2015.

* cited by examiner

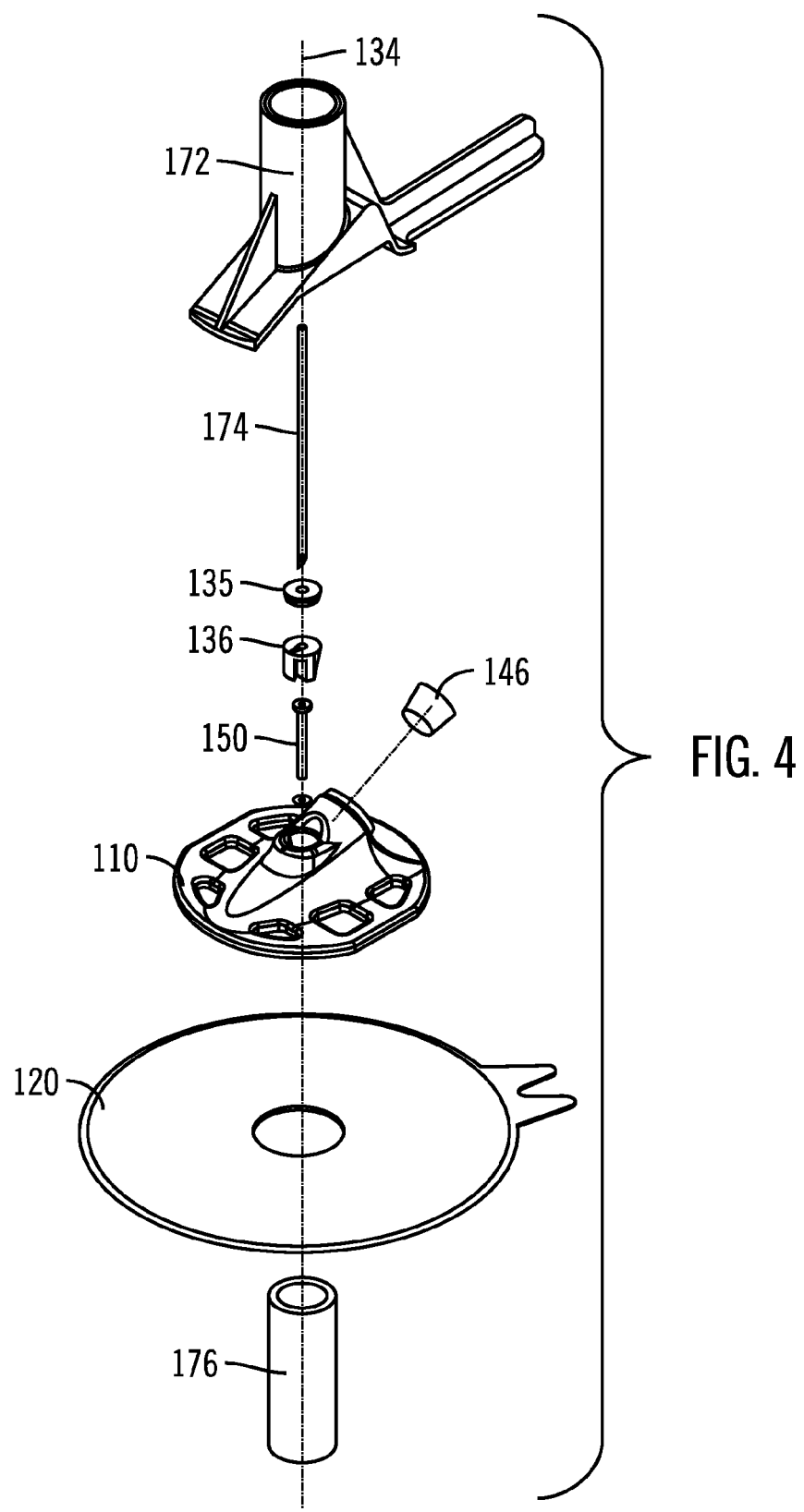

ON-BODY INJECTOR AND METHOD OF USE

CROSS REFERENCES TO RELATED APPLICATIONS

This application is a continuation of and claims the benefit of U.S. patent application Ser. No. 14/613,605, filed on Feb. 4, 2015, entitled ON-BODY INJECTOR AND METHOD OF USE, which is a continuation of and claims the benefit of U.S. patent application Ser. No. 14/134,749, filed on Dec. 19, 2013, now U.S. Pat. No. 8,979,808, entitled ON-BODY INJECTOR AND METHOD OF USE, which is a continuation-in-part of and claims the benefit of U.S. patent application Ser. No. 14/052,929, filed on Oct. 14, 2013, entitled THERAPEUTIC AGENT INJECTION DEVICE, all of which are incorporated by reference in their entireties herein.

TECHNICAL FIELD

The technical field of this disclosure is personal medical systems, particularly, on-body injectors and methods of use.

BACKGROUND OF THE INVENTION

Certain medical conditions or diseases require that patients intermittently inject a drug or therapeutic agent subcutaneously to maintain the medical condition or disease under control. Multiple daily injections (MDIs) may be required. One such medical condition is diabetes, for which insulin is injected to regulate blood glucose. An estimated twenty-six million people in the United States, or about 8% of the population, have diabetes. This percentage is expected to increase in the near-term as the population ages.

Certain patients are unlikely or unable to follow the drug regimen required to maintain their medical condition under control. Some patients are squeamish about injecting the drug themselves and others suffer adverse effects from repeated injections, such as bruising at the injection site. To accommodate such patients, injection ports have been developed which only require that the patient puncture their skin every few days to install an injection port, rather than injecting with a needle into their skin numerous times a day. Injection ports employ a cannula inserted subcutaneously, and the patient injects the drug into the injection port adhering to their skin rather than directly into their cutaneous tissue.

Unfortunately, injection ports still require that the patient administer the therapeutic agent repeatedly throughout the day. Injection ports with dedicated reservoirs allowing bolus injection have been developed, but maintain a continuous flow path and run the risk of inadvertent bolus injection. Although these problems can be remedied with a dedicated electronic insulin pump, many patients are unwilling or unable to use a dedicated insulin pump due to the expense and complication. Such systems present other obstacles to the patient, such as the inability to choose different therapy options based on specific daily needs or activity.

It would be desirable to have an on-body injectors and methods of use that would overcome the above disadvantages.

SUMMARY OF THE INVENTION

One aspect of the invention provides an on-body injector for use with a patient with an injection device having an injection port in fluid communication with a delivery tube and the injection port lying on an injection axis. The on-body injector includes a bolus reservoir; a bolus injection needle in fluid communication with the bolus reservoir, the bolus injection needle having a bolus injection needle tip aligned with the injection port, the bolus injection needle being slideably biased away from the injection port to define a gap between the bolus injection needle tip and the injection port; and a button operably connected to the bolus injection needle to slide the bolus injection needle along the injection axis. The button is operable to advance the bolus injection needle tip to close the gap and advance the bolus injection needle tip into the injection port to form an injection flow path from the bolus reservoir, through the bolus injection needle, through the delivery tube, and into the patient. The button is further operable to advance a plunger through the bolus reservoir to deliver a predetermined bolus volume to the patient through the injection flow path.

Another aspect of the invention provides an on-body injector for use with a patient with an injection device having an introducer port in fluid communication with a delivery tube. The on-body injector includes a pressurized reservoir; a flow restrictor disposed between the pressurized reservoir and the delivery tube, the flow restrictor being tubing having a length and interior diameter selected to provide a desired pressure drop; and a fill port in fluid communication with the pressurized reservoir.

Another aspect of the invention provides a method of use for an on-body injector with an injection device for delivering a predetermined bolus volume to a patient, the method including deploying the injection device in the patient, the injection device having a delivery tube placed in the patient and an injection port in fluid communication with the delivery tube; securing the on-body injector to the injection device, the on-body injector having a bolus injection needle aligned with and spaced apart from the injection port; depressing a button on the on-body injector to advance the bolus injection needle into the injection port; and further depressing the button to deliver the predetermined bolus volume from the on-body injector through the bolus injection needle, through the delivery tube, and into the patient.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 1-4 are perspective, section, perspective, and exploded perspective views, respectively, of one embodiment of an injection device made in accordance with the invention.

DETAILED DESCRIPTION

FIGS. 1-5C, in which like elements share like reference numbers, are various views of one embodiment of an injection device made in accordance with the invention. The injection device includes an introducer port along an introducer axis and an injection port along an injection axis, with the injection axis being non-collinear with the introducer axis. In this embodiment, the injection axis is at an angle to and intersects with the introducer axis.

Figure 1:
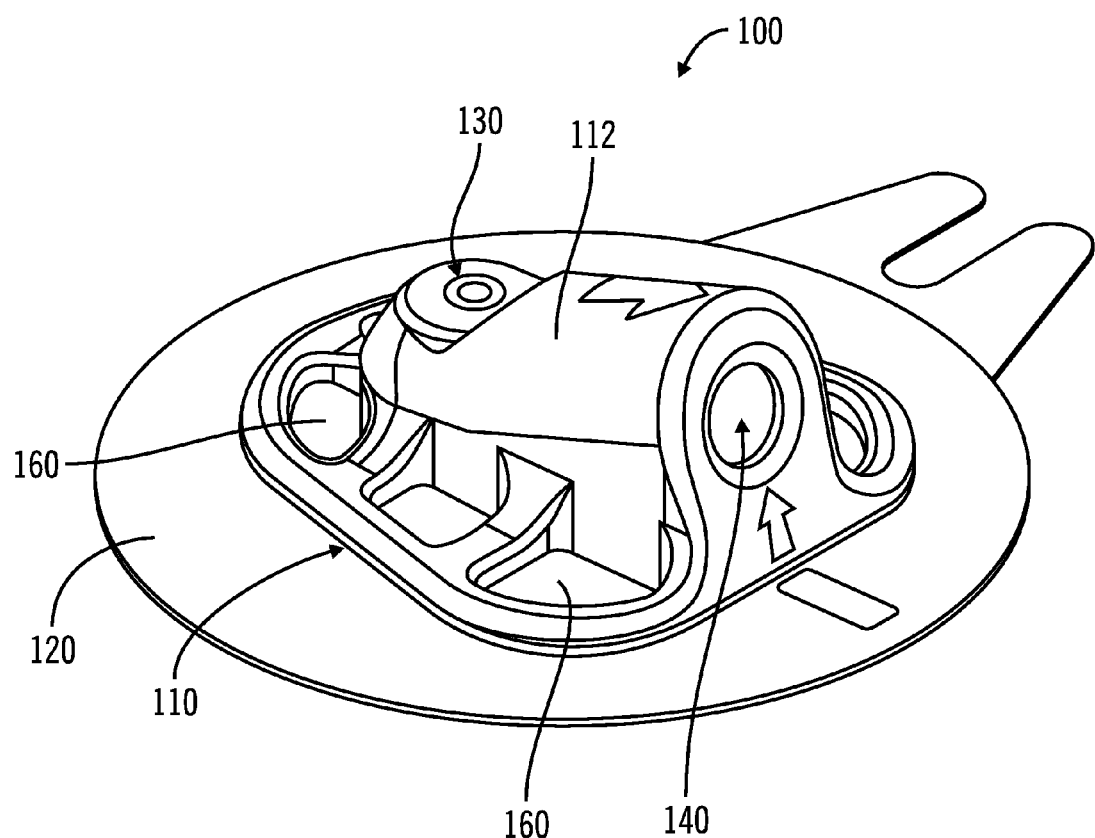

FIG. 1 is a perspective view of the injection device 100 including a body 110 and a patch 120 attached to the body 110. The patch 120 is operable to adhesively attach the injection device 100 to a patient (not shown). The body 110 has a port face 112, with an introducer port 130 and an injection port 140 on the port face 112. The introducer port 130 is used to place a delivery tube subcutaneously in the patient. The injection port 140 is used by the patient to inject a therapeutic agent, which as defined herein can be any liquid such as a liquid including a therapeutic agent, drug, diagnostic agent, or the like. The body 110 also includes cutouts 160. Those skilled in the art will appreciate that the introducer port 130 can be too small to be effectively used by a patient for injection, but could be used to inject a therapeutic agent, such as a bolus injection using a mechanically attached device, as desired for a particular application.

Figure 2:
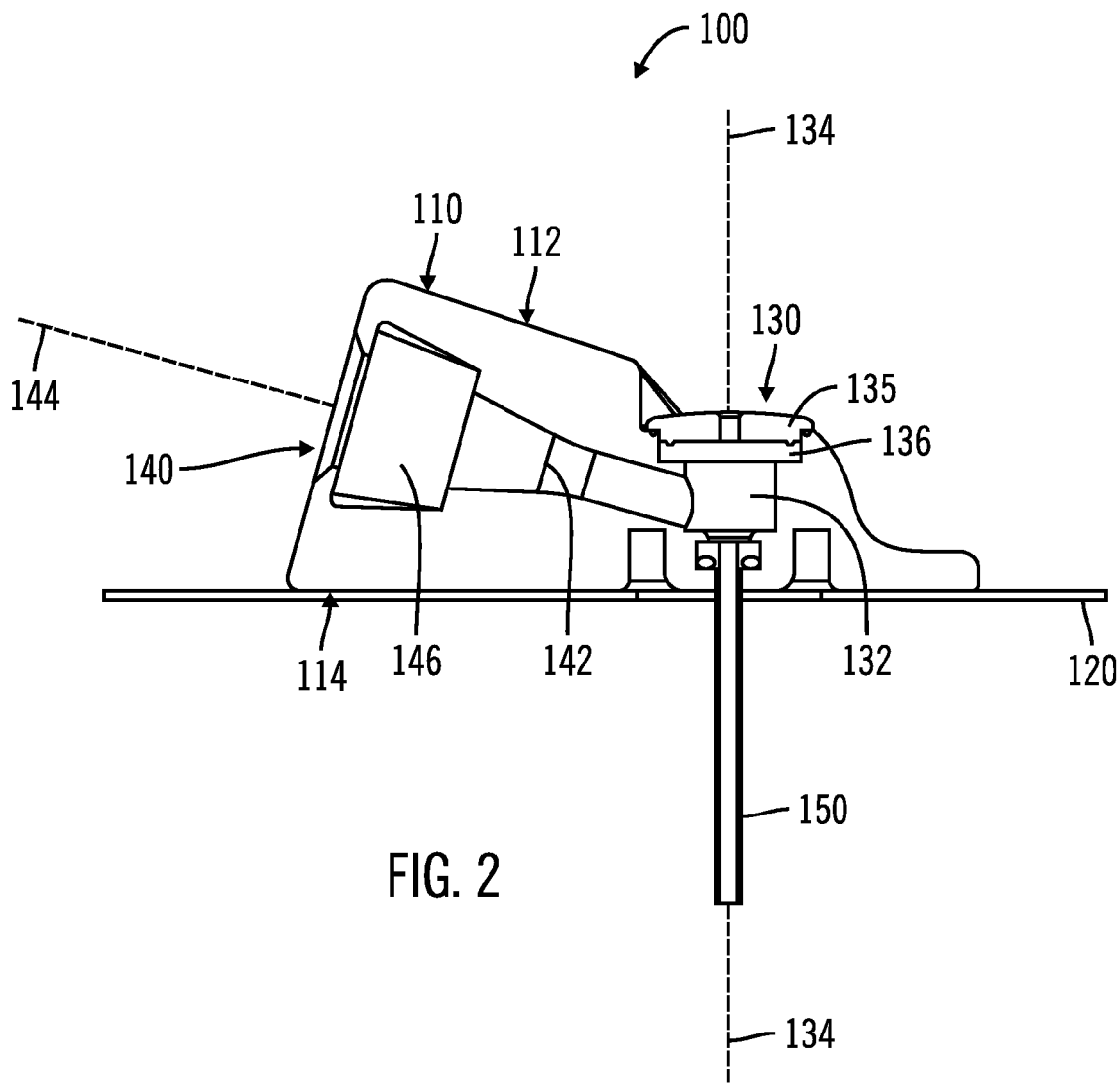

FIG. 2 is a section view of the injection device 100, the section bisecting the introducer port 130 and the injection port 140, and includes the introducer axis 134 and injection axis 144. An axis as defined herein generally follows the centerline of an associated channel through an associated port. The body 110 has a port face 112 and a patient face 114. A delivery tube 150 for subcutaneous delivery of the therapeutic agent projects from and is generally perpendicular to the patient face 114. The delivery tube 150 is operably connected to the introducer port 130 and defines an introducer axis 134 along the introducer channel 132, the delivery tube 150 being in fluid communication with the injection port 140. The introducer port 130 includes an introducer channel 132, with an introducer port cover 135 and an introducer septum 136 disposed in the introducer channel 132. The injection port 140 includes an injection channel 142 defining an injection axis 144 with an injection septum 146 disposed in the injection channel 142. In one embodiment, the introducer septum 136 and/or the injection septum 146 is self sealing, such that each of the septums block fluid flow through the septum after a needle has been put through the septum then removed, preventing fluid flow from the port. In this embodiment, the injection axis 144 is at an angle to and intersects with the introducer axis 134. In one example, the delivery tube 150 is a flexible cannula and a needle hub assembly can be used to place the delivery tube 150 subcutaneously in the patient. In another example, the delivery tube 150 is a rigid needle and the delivery tube 150 can be placed subcutaneously in the patient with or without a needle hub assembly.

Figure 3:
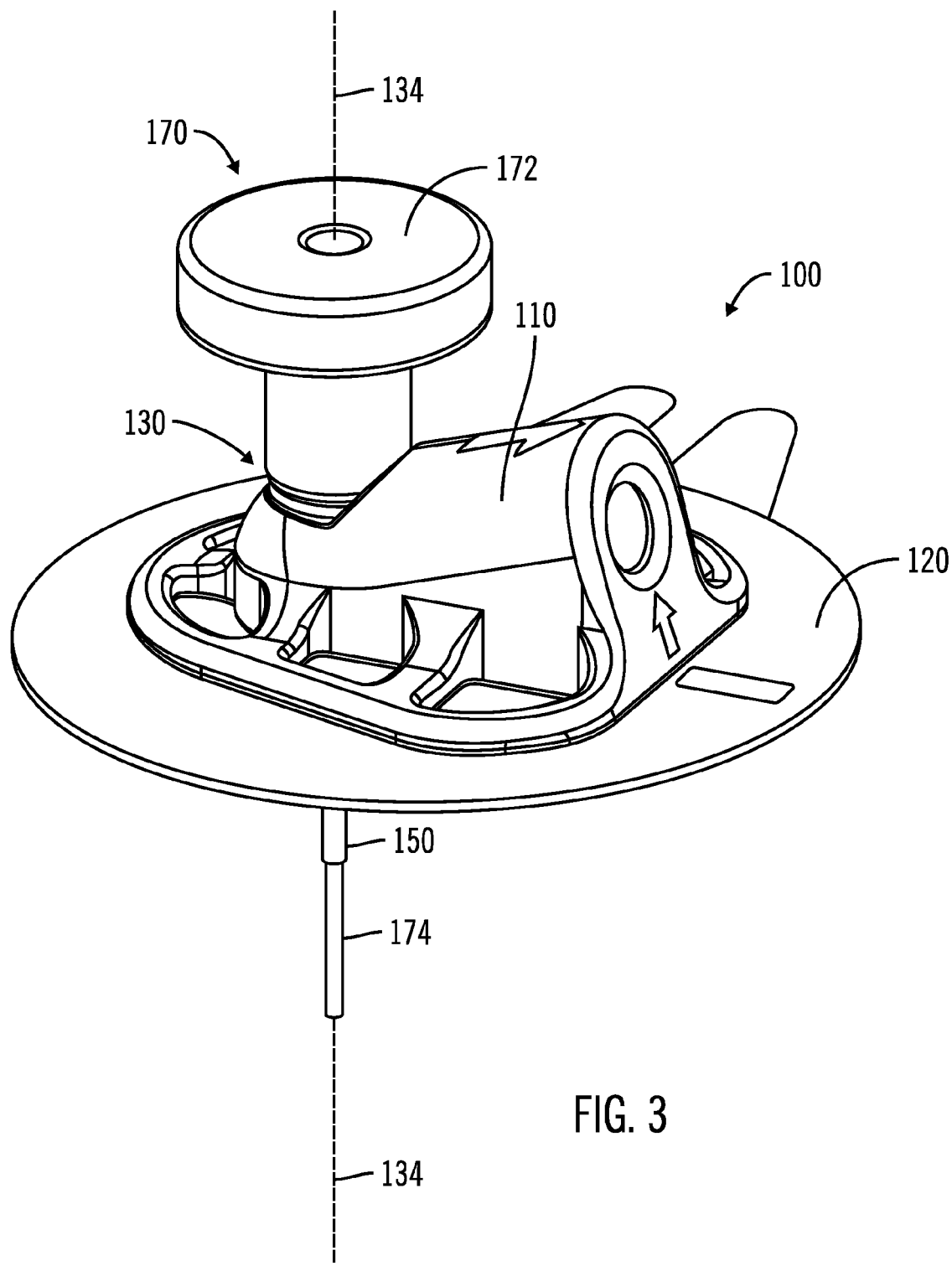

FIG. 3 is a perspective view of the injection device 100 with a needle hub assembly 170. The needle hub assembly 170 includes a needle hub 172 and a needle 174 attached to the needle hub 172. The needle 174 of the needle hub assembly 170 is inserted through the introducer port 130 and through the delivery tube 150 along the introducer axis 134. The needle hub assembly 170 can be used to add rigidity to the delivery tube 150 during implantation when the delivery tube 150 is a flexible cannula.

FIG. 4 is an exploded perspective view of the injection device with a needle hub assembly. A needle guard 176 disposed around the needle 174 can be used to protect the needle 174 and the delivery tube 150 when the injection device and needle hub assembly are assembled for shipping. The various parts of the injection device and needle hub assembly can be connected by interference fit, adhesive, welding, and/or any other method of attachment suitable for a particular application.

Figure 5A:
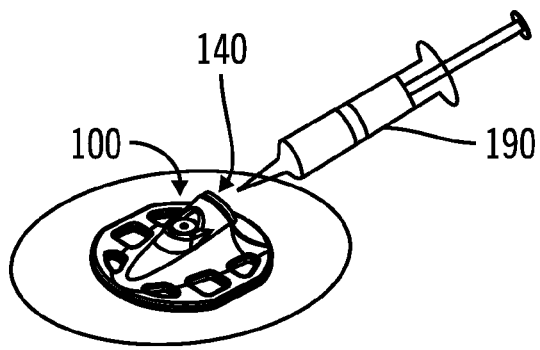
FIGS. 5A-5C are perspective views of one embodiment of an injection device made in accordance with the invention.
Figure 5B:
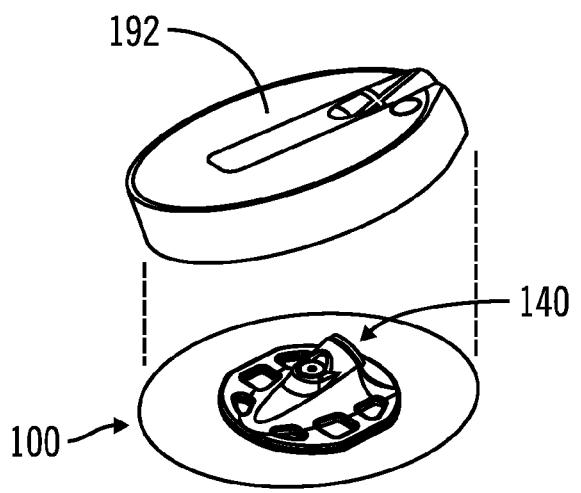
Figure 5C:
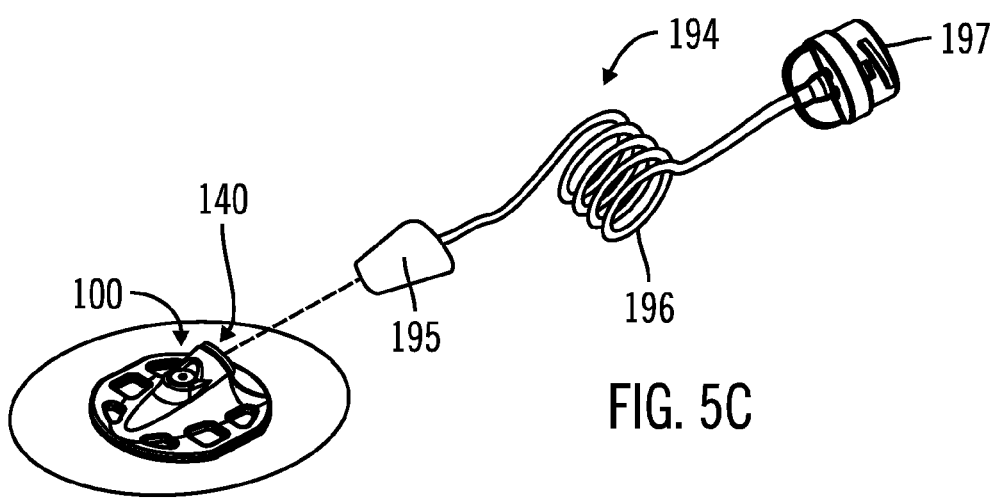

FIGS. 5A-5C are perspective views of various applications of the injection device made in accordance with the invention. Referring to FIG. 5A, a syringe 190 can be used to deliver a therapeutic agent through the injection port 140 of the injection device 100. The syringe can be a conventional syringe, a standard insulin pen, or a needleless syringe. The needle length of a conventional syringe or standard insulin pen can be of any length because the injection axis is non-collinear with the introducer axis, such that a longer needle does not damage the injection device. In one embodiment, the injection port 140 is adapted to be mateable with the syringe 190, with a socket, fitting, or the like, to increase ease of use. In one example, the injection port 140 is a socket with a socket needle which pierces a foil front end of a needleless syringe when the needleless syringe is seated in the socket. The needleless syringe itself has no needle in this example.

Referring to FIG. 5B, an on-body injector 192 is mateable with the injection port 140 of the injection device 100 and can be used to deliver a therapeutic agent through the injection port 140. The on-body injector 192 can include a reservoir to hold the therapeutic agent. In one embodiment, the on-body injector 192 can deliver a basal and/or bolus dose of the therapeutic agent.

Referring to FIG. 5C, an extendable tube 194 can be used to deliver a therapeutic agent through the injection port 140. The extendable tube 194 includes a port connector 195, a tube 196, and an external device fitting 197, all being in fluid communication. The port connector 195 is in fluid communication with the injection port 140 with a needle or mateable fitting to deliver the therapeutic agent through the injection port 140. The external device fitting 197 is connectable to an external device, such as a wearable insulin pump or an infusion tubing line to a gravity fed container.

Figure 6:
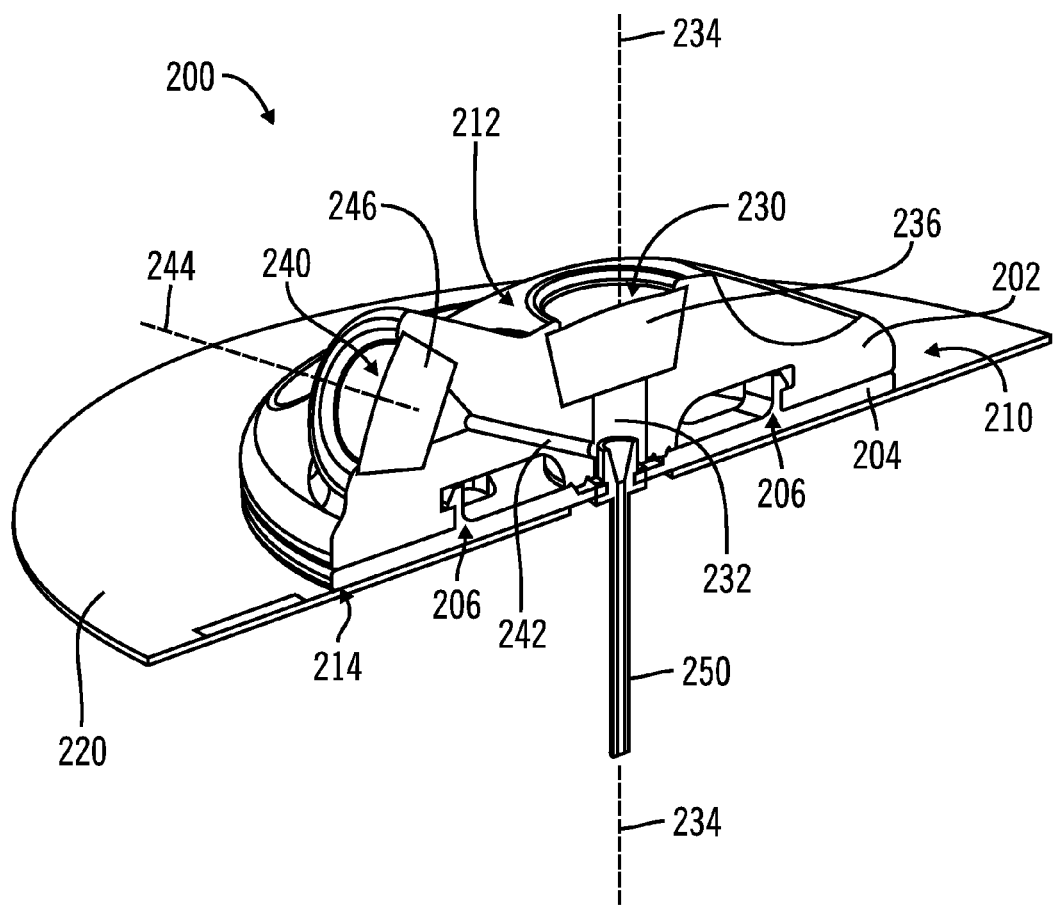
FIG. 6 is a section perspective view of one embodiment of an injection device made in accordance with the invention.

FIG. 6 is a section perspective view of one embodiment of an injection device made in accordance with the invention. In this embodiment, an upper body portion is rotatable about the introducer axis independent of a lower body portion, so that the injection axis can be positioned at a desired rotary angle regardless of the initial placement of the patch on the patient. This allows the patient to select a rotary position for the injection port that is convenient for injection of the therapeutic agent.

The body of the injection device can have a first body portion including the port face and a second body portion including the patient face, the first body portion and the second body portion being rotatably connected with a flange, the first body portion and the second body portion being independently rotatable about the introducer axis.

The body 210 of the injection device 200 includes an upper body portion 202 and a lower body portion 204. The upper body portion 202 and lower body portion 204 are rotatably connected with a flange 206 so that the upper body portion 202 and the lower body portion 204 can rotate independently about the introducer axis 234 defined by the delivery tube 250 along the introducer channel 232. The upper body portion 202 has a port face 212 and the lower body portion 204 has a patient face 214. A patch 220 is attached to the patient face 214 and is operable to adhesively attach the injection device 100 to a patient (not shown).

The delivery tube 250 for subcutaneous delivery of a therapeutic agent projects from and is generally perpendicular to the patient face 214. The delivery tube 250 is operably connected to the introducer port 230, the delivery tube 250 being in fluid communication with the injection port 240. The introducer port 230 includes an introducer channel 232, with an introducer septum 236 disposed in the introducer channel 232. The injection port 240 includes an injection channel 242 defining an injection axis 244 with an injection septum 246 disposed in the injection channel 242.

The injection axis 244 is non-collinear with the introducer axis 234. In this embodiment, the injection axis 244 is at an angle to and intersects with the introducer axis 234. In one example, the delivery tube 250 is a flexible cannula and a needle hub assembly can be used to place the delivery tube 250 subcutaneously in the patient. In another example, the delivery tube 250 is a rigid needle and the delivery tube 250 can be placed subcutaneously in the patient with or without a needle hub assembly.

In operation, the patch 220 is attached to the patient and the delivery tube 250 inserted in the patient for subcutaneous delivery of a therapeutic agent. The injection port 240 in the upper body portion 202 can be rotated about the introducer axis 234 even though the lower body portion 204 is at a fixed position on the patient since the lower body portion 204 is attached to the patient by the patch 220.

FIGS. 7-11, in which like elements share like reference numbers, are various views of one embodiment of an injection device made in accordance with the invention. The injection device includes an introducer port along an introducer axis and an injection port along an injection axis, with the injection axis being non-collinear with the introducer axis. In this embodiment, the injection axis is parallel to and does not intersect with the introducer axis.

The injection device for delivering a therapeutic agent to a patient can include a body, the body having a patient face and a port face opposite the patient face, the port face having an introducer port including an introducer channel and an injection port including an injection channel, the introducer channel being in fluid communication with the injection channel through a cross channel, the injection channel defining an injection axis; a delivery tube for subcutaneous delivery of the therapeutic agent to the patient, the delivery tube projecting from and being generally perpendicular to the patient face, the delivery tube defining an introducer axis and being in fluid communication with the injection port; and a patch, the patch being attached to the patient face and being operable to adhesively attach to the patient; wherein the injection axis is parallel to the introducer axis.

Figure 7:
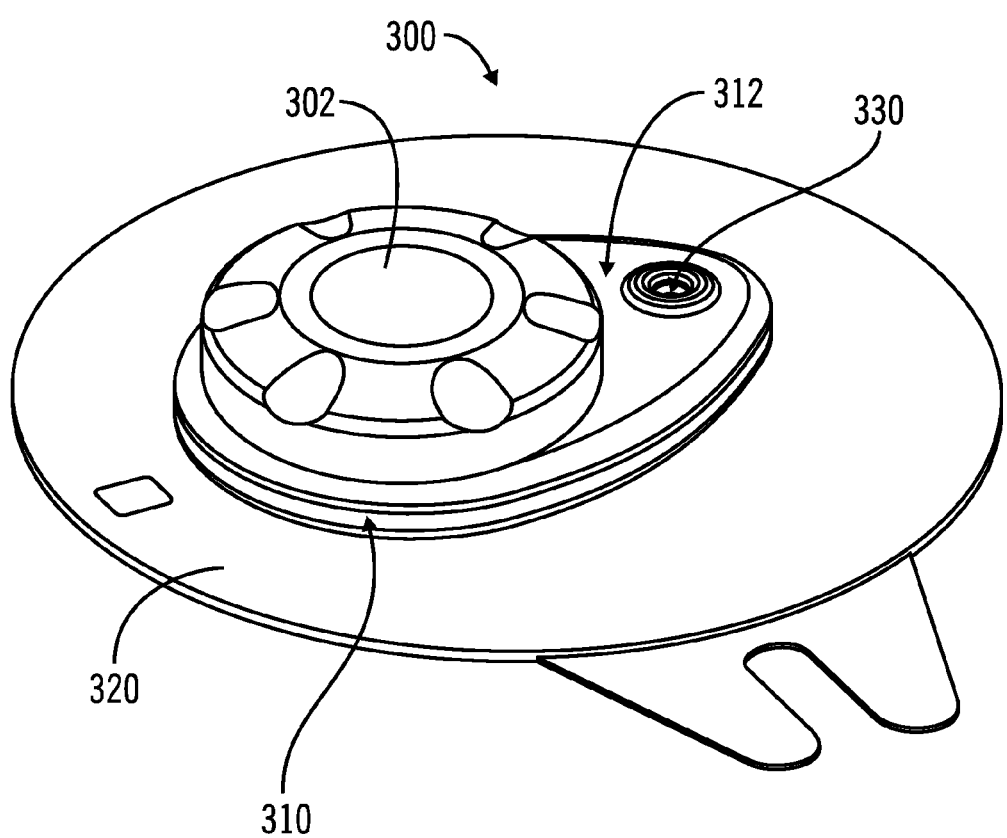
FIGS. 7-11 are perspective, perspective, section, section, and perspective section views, respectively, of one embodiment of an injection device made in accordance with the invention.

FIG. 7 is a perspective view of the injection device 300 including a body 310 and a patch 320 attached to the body 310. The patch 320 is operable to adhesively attach the injection device 300 to a patient (not shown). The body 310 has a port face 312, with an introducer port 330 on the port face 312. The introducer port 330 is used to place a delivery tube subcutaneously in the patient. In this example, an optional injection cap 302 secured to the body 310 to protect an injection port, which is used by the patient to inject a therapeutic agent.

Figure 8:
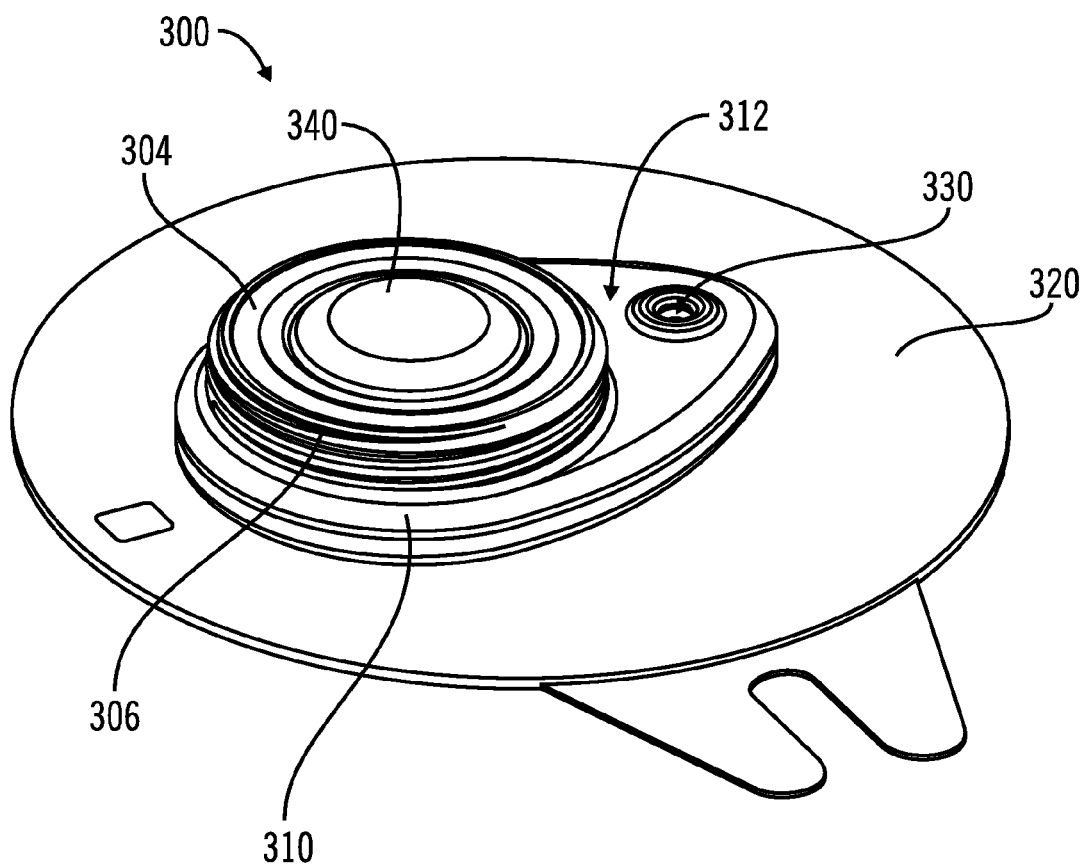

FIG. 8 is a perspective view of the injection device 300 with the optional injection cap removed to expose the injection port 340. In this example, the body 312 includes threads 306 to secure the optional injection cap to the body and an optional O-ring 304 to seal the area around the injection port 340 when the optional injection cap is secured to the body.

Figure 9:
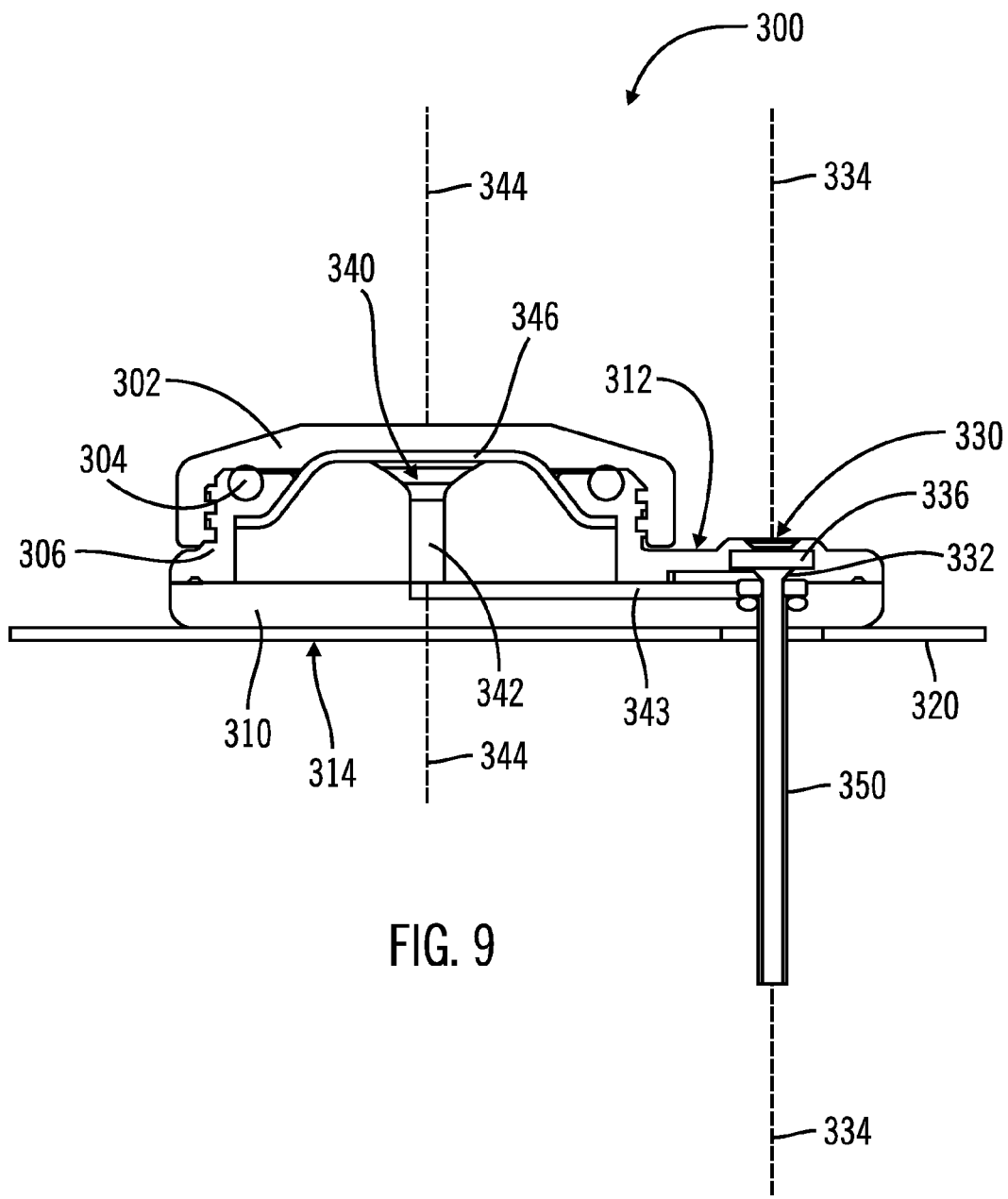

FIG. 9 is a section view of the injection device 300, the section bisecting the introducer port 330 and the injection port 340 and including the introducer axis 334 and injection axis 344. The body 310 has a port face 312 and a patient face 314. A delivery tube 350 for subcutaneous delivery of the therapeutic agent projects from and is generally perpendicular to the patient face 314. The delivery tube 350 is operably connected to the introducer port 330 and defines an introducer axis 334 along the introducer channel 332, the delivery tube 350 being in fluid communication with the injection port 340. The introducer port 330 includes an introducer channel 332, with an introducer septum 336 disposed in the introducer channel 332. The injection port 340 includes an injection channel 342 defining an injection axis 344 with an injection septum 346 disposed over the injection channel 342. In this embodiment, the injection axis 344 is parallel to and does not intersect with the introducer axis 334. A cross channel 343 connects the injection channel 342 to the introducer channel 332. In one example, the delivery tube 350 is a flexible cannula and a needle hub assembly can be used to place the delivery tube 350 subcutaneously in the patient. In another example, the delivery tube 350 is a rigid needle and the delivery tube 350 can be placed subcutaneously in the patient with or without a needle hub assembly.

Figure 10:
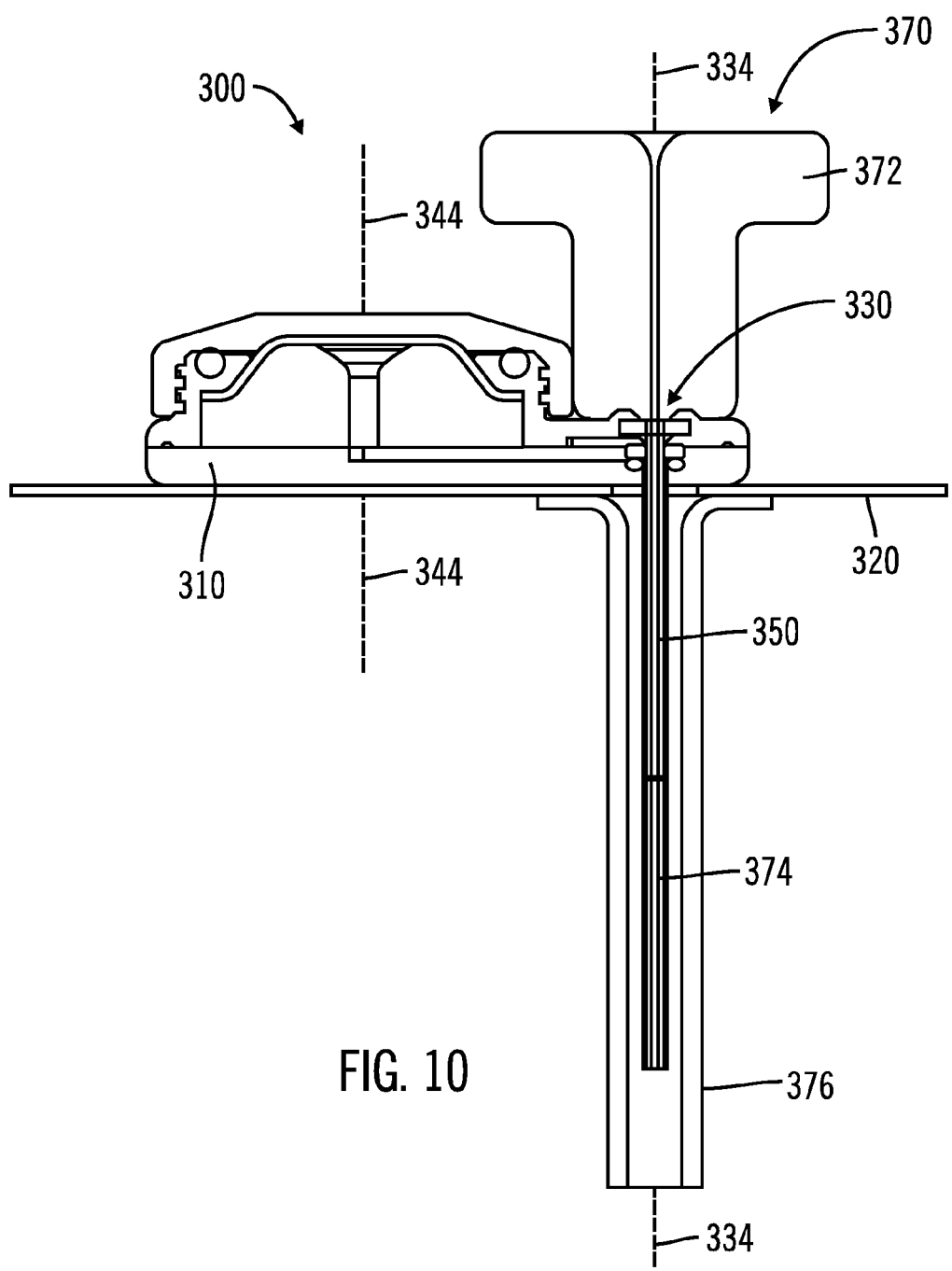

FIG. 10 is a section view of the injection device 300 with a needle hub assembly 370 and a needle guard 376. The needle hub assembly 370 includes a needle hub 372 and a needle 374 attached to the needle hub 372. The needle 374 of the needle hub assembly 370 is inserted through the introducer port 330 and through the delivery tube 350 along the introducer axis 334. The needle hub assembly 370 can be used to add rigidity to the delivery tube 350 when the delivery tube 350 is a flexible cannula. The needle hub assembly 370 can optionally be used when the delivery tube 350 is a rigid needle. A needle guard 376 disposed around the needle 374 can be used to protect the needle 374 and the delivery tube 350 when the injection device and needle hub assembly are assembled for shipping.

Figure 11:
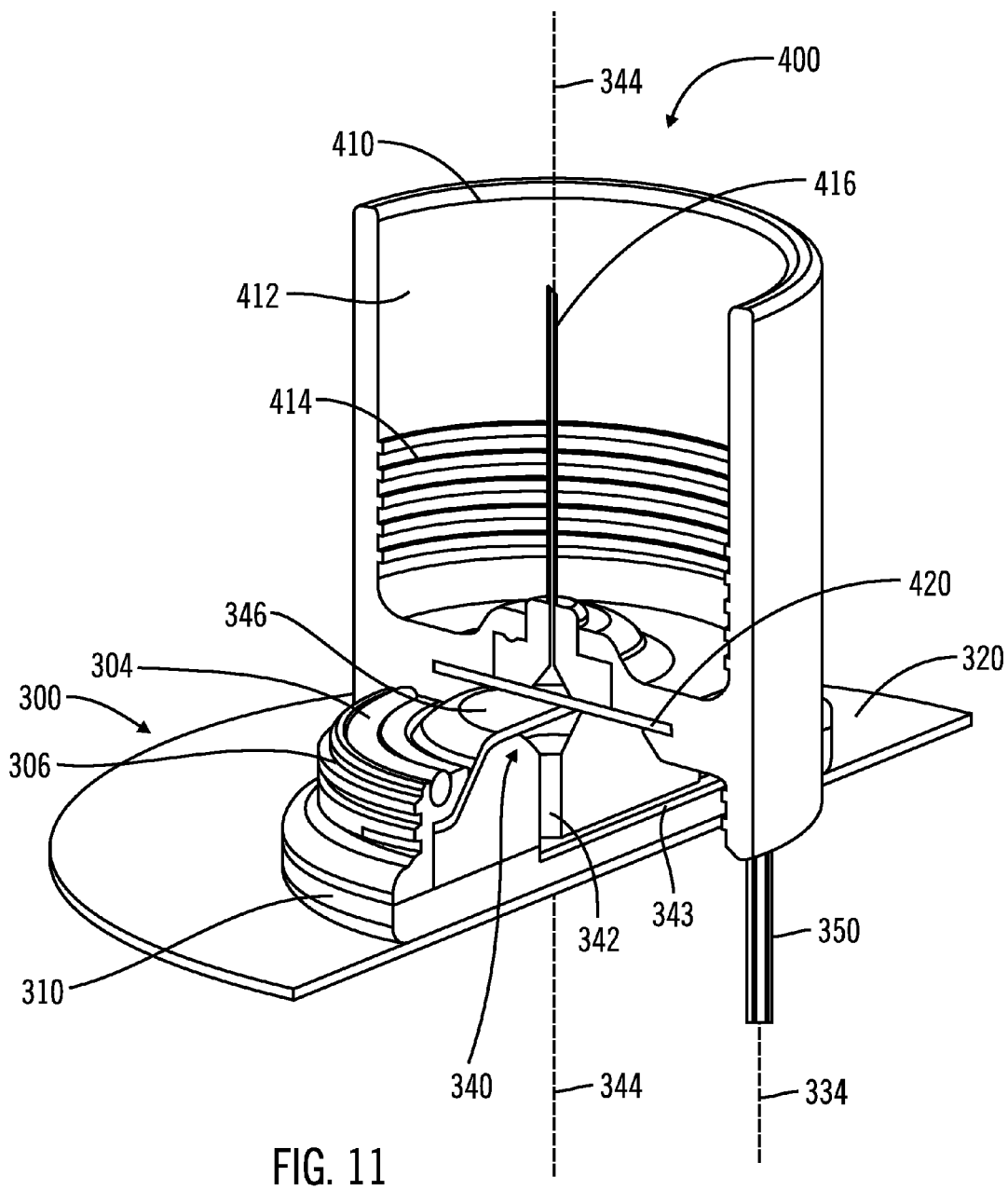

FIG. 11 is a perspective section view of the injection device with an injection adapter assembly. For clarity of illustration, the cross section cut of the injection device 300 in the illustration bisects the introducer port 330 and the injection port 340, and includes the introducer axis 334 and injection axis 344. The cross section cut of the injection adapter assembly 400 in the illustration includes the injection axis 344 and is perpendicular to the section of the injection device 300. The injection adapter assembly 400 screws onto the injection device 300 using the threads 306 on the body 310 to secure the needleless pen injector to the body 310, with the O-ring 304 sealing around the interface between the adapter septum 420 and the injector septum 346. Those skilled in the art will appreciate that the mateable connection securing the needleless pen injector to the body is not limited to threads and can be any mateable connection desired for a particular application.

In this embodiment, the injection adapter assembly 400 is adapted to receive a needleless pen injector (not shown). The adapter body 410 defines a recess 412 adapted to receive a tip of the needleless pen injector. In this example, the needleless pen injector includes threads on its outer diameter complementary to the adapter threads 414 on the inner diameter of the adapter body 410. The tip of the needleless pen injector is screwed into the recess 412 so that the adapter needle 416 is received in the needleless pen injector, accessing the therapeutic agent contained within the needleless pen injector by piercing a foil on the tip of the needleless pen injector or accessing a pen injector port adapted to receive the adapter needle 416. With the needleless pen injector secured in the injection adapter assembly 400, pressure applied to the therapeutic agent enclosed in the needleless pen injector forces the therapeutic agent through the adapter needle 416 and the adapter septum 420 into the injection device 300, where the therapeutic agent passes through the injector septum 346 into the injection port 340, through the injection channel 342, the cross channel 343, and the delivery tube 350, and into the patient.

Those skilled in the art will appreciate that a variety of interfaces can be used between the needleless pen injector, the injection adapter assembly 400, and the injection device 300. In the embodiment of FIG. 11, the adapter septum 420 and the injector septum 346 are permeable so that the therapeutic agent passes through the adapter septum 420 and the injector septum 346. The septums can be hydrophilic when used with the needleless pen injector to allow the therapeutic agent to pass through. In another embodiment, the injector septum can include a slit valve operable to open on receiving a stub tube at the tip of the needleless pen injector. In yet another embodiment, the injector septum can include a slit valve which is open by a mechanical lever that pushes open and spread the slit valve when the needleless pen injector is received in the injection adapter assembly. In yet another embodiment, the needleless pen injector is interlocked with the injection adapter assembly so that no therapeutic agent can be dispensed from the needleless pen injector until the needleless pen injector is fully engaged with the injection adapter assembly.

FIGS. 12A-12D are various views of needleless pen injectors for use with an injection device made in accordance with the invention. Each of the needleless pen injectors is provided with a manual or automatic pressurization to force the therapeutic agent held within the needleless pen injector into the injection device and patient, once the needleless pen injector has been fully engaged with an injection adapter assembly.

Figure 12A:
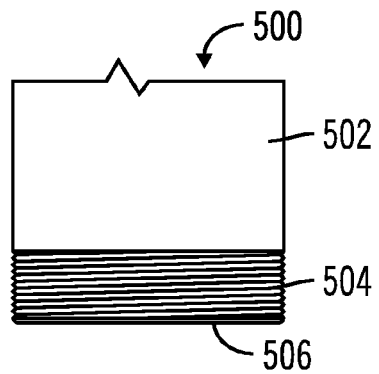
FIGS. 12A-12D are side and section views of needleless pen injectors for use with an injection device made in accordance with the invention.
Figure 12B:
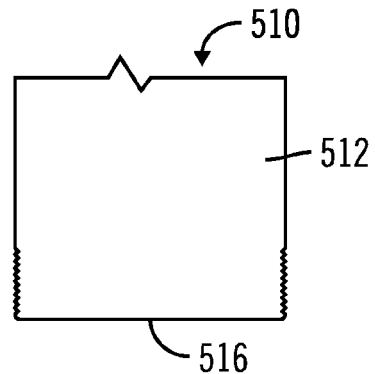
Figure 12C:
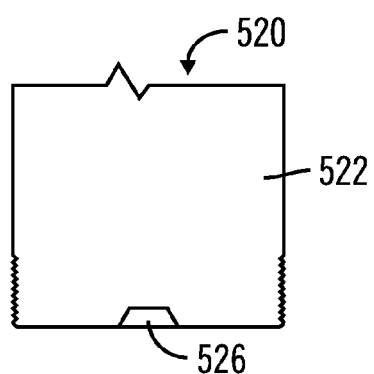
Figure 12D:
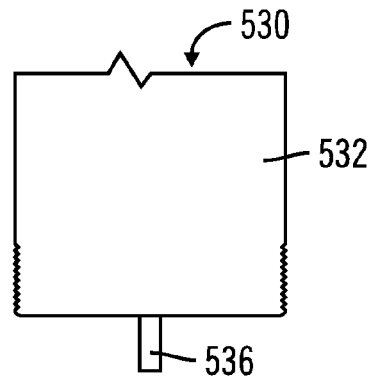

FIG. 12A is a side view of the tip of a needleless pen injector 500 having a barrel 502 to contain a therapeutic agent and optional threads 504 for use with an adapter body having threads on the inner diameter. The end 506 of the needleless pen injector 500 can be adapted to accommodate the particular design of an injection adapter assembly for a particular application. FIG. 12B is a section view of the tip of a needleless pen injector 510 having a barrel 512 to contain a therapeutic agent and a foil 516 across the end of the needleless pen injector 510. The foil 516 can be pierced by an adapter needle in the injection adapter assembly (shown in FIG. 11) to provide fluid communication between the needleless pen injector 510 and the injection device through the injection adapter assembly. FIG. 12C is a section view of the tip of a needleless pen injector 520 having a barrel 522 to contain a therapeutic agent and a pen port 526 at the end of the needleless pen injector 520. The pen port 526 can receive an adapter needle in the injection adapter assembly (shown in FIG. 11) to open the pen port 526 and provide fluid communication between the needleless pen injector 520 and the injection device through the injection adapter assembly. FIG. 12D is a section view of the tip of a needleless pen injector 530 having a barrel 532 to contain a therapeutic agent and a stub tube 536 at the end of the needleless pen injector 530. The stub tube 536 is operable to open a slit valve on the injector septum of the injection device.

FIGS. 13A-13F, in which like elements share like reference numbers, are section views of pop-up indicator ports for use with an injection device made in accordance with the invention. Because the introducer port and the injection port of the injection device are both in fluid communication with the delivery tube, flow blockage in the delivery tube can cause an increase in pressure at both ports when the patient attempts to inject a therapeutic agent. The flow blockage/pressure increase can be detected by the patient, indicating that the therapeutic agent is not being delivered, with a pop-up indicator port in the port not being used for injection. During injection, the membrane of the pop-up indicator port is close to the body of the injection device under normal conditions, and extends from the body of the injection device when the delivery tube is blocked and the pressure increases above a predetermined pressure.

The pop-up indicator can be disposed in the introducer channel, the pop-up indicator having a normal state when pressure in the introducer channel is normal and an alarm state when pressure in the introducer channel exceeds a predetermined value.

Figure 13A:
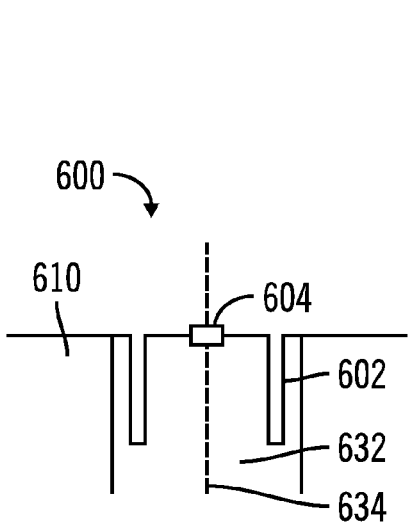
FIGS. 13A-13F are section views of pop-up indicator ports for use with an injection device made in accordance with the invention.
Figure 13B:
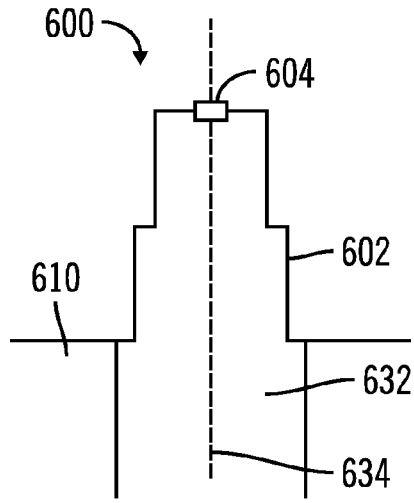

FIGS. 13A & 13B are section views of a pop-up indicator port 600 with a folded membrane 602 installed in the introducer port. The pop-up indicator port 600 is installed in the introducer channel 632 of the body 610 along the introducer axis 634, and is in fluid communication with the injection channel. A self-closing port 604 in the membrane 602 allows a needle of a needle hub assembly to pass through the membrane 602 when a needle hub assembly is used to implant the injection device. No self-closing port is required if a needle hub assembly is not used to implant the injection device. Referring to FIG. 13A, the pop-up indicator port 600 is in the normal state with normal pressure in the introducer channel 632, with the membrane 602 folded on itself. Referring to FIG. 13B, the pop-up indicator port 600 is in the alarm state due to pressure in the introducer channel 632 exceeding a predetermined value. The pressure occurs when a therapeutic agent is being injected into the injection port, which is in fluid communication with the introducer channel 632, while the delivery tube is blocked. In the alarm state, the membrane 602 unfolds to extend from the body 610.

Figure 13C:
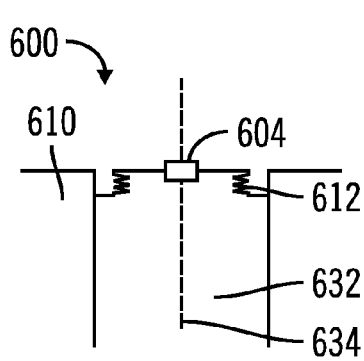
Figure 13D:
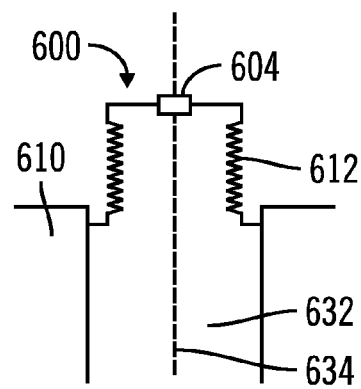

FIGS. 13C & 13D are section views of a pop-up indicator port 600 with an accordion membrane 612 installed as the introducer port. Referring to FIG. 13C, the pop-up indicator port 600 is in the normal state with normal pressure in the introducer channel 632, with the membrane 612 pleated like an accordion. Referring to FIG. 13D, the pop-up indicator port 600 is in the alarm state due to pressure in the introducer channel 632 exceeding a predetermined value. The pressure occurs when a therapeutic agent is being injected into the injection port, which is in fluid communication with the introducer channel 632, while the delivery tube is blocked. In the alarm state, the membrane 612 uncompresses the pleats to extend from the body 610.

Figure 13E:
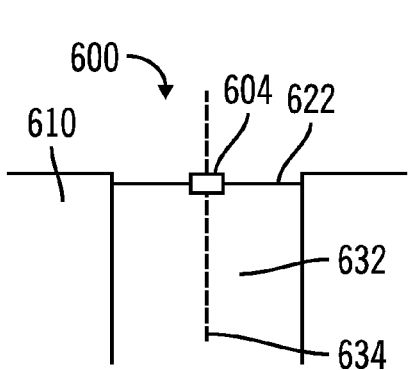
Figure 13F:
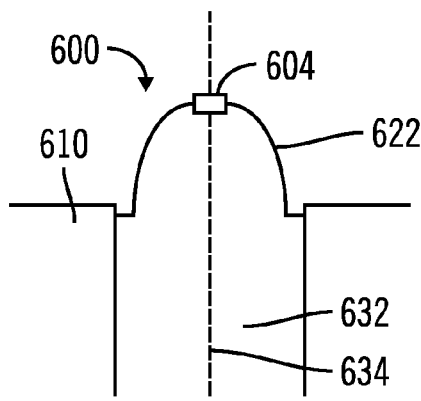

FIGS. 13E & 13F are section views of a pop-up indicator port 600 with a deformable membrane 622 installed as the introducer port. Referring to FIG. 13E, the pop-up indicator port 600 is in the normal state with normal pressure in the introducer channel 632, with the membrane 622 extending across the introducer channel 632. Referring to FIG. 13F, the pop-up indicator port 600 is in the alarm state due to pressure in the introducer channel 632 exceeding a predetermined value. The pressure occurs when a therapeutic agent is being injected into the injection port, which is in fluid communication with the introducer channel 632, while the delivery tube is blocked. In the alarm state, the material of the membrane 622 deforms under pressure to extend from the body 610. In another embodiment, the material of the membrane 622 can deforms sufficiently to allow the therapeutic agent to leak through the membrane 622, providing additional indication of the high pressure and delivery tube blockage.

Those skilled in the art will appreciate that the material and dimensions of the parts of the membrane (folds and/or pleats) can be selected as desired for a particular application. In one embodiment, the material is resilient, so that the membrane returns to the normal state after being in the alarm state. In another embodiment, the material is deformable so that the membrane remains extending from the body after the pressure is relieved and the alarm state clears. The extended membrane reminds the patient of the delivery tube blockage and the need to replace the injection device. Exemplary materials for the membrane include silicone rubber or the like.

Figure 14A:
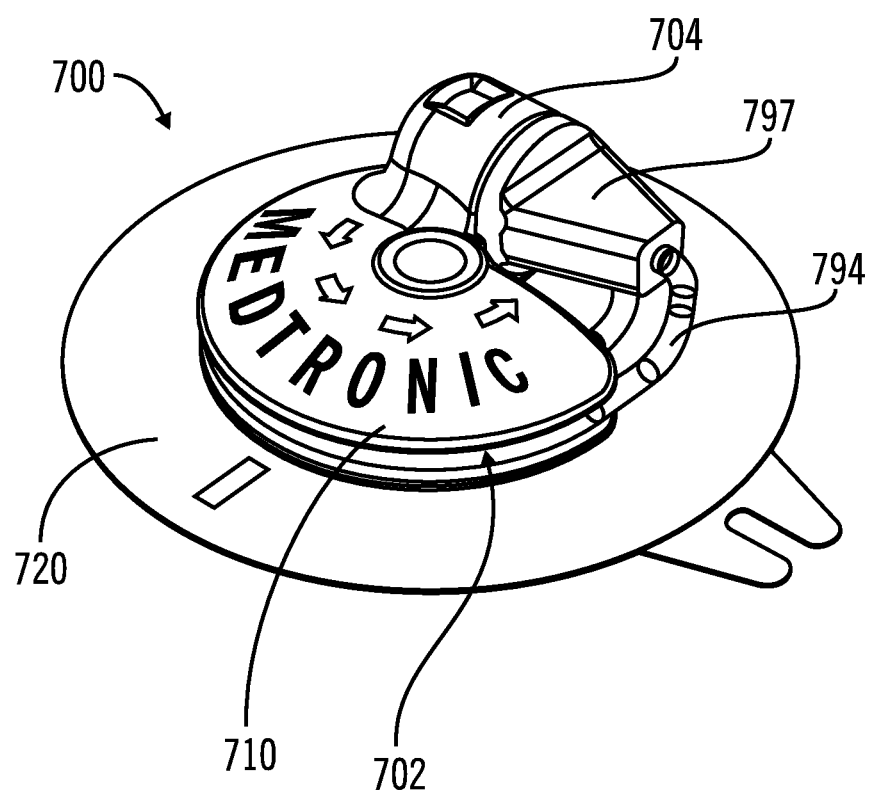
FIGS. 14A & 14B are perspective views of one embodiment of an injection device made in accordance with the invention.
Figure 14B:
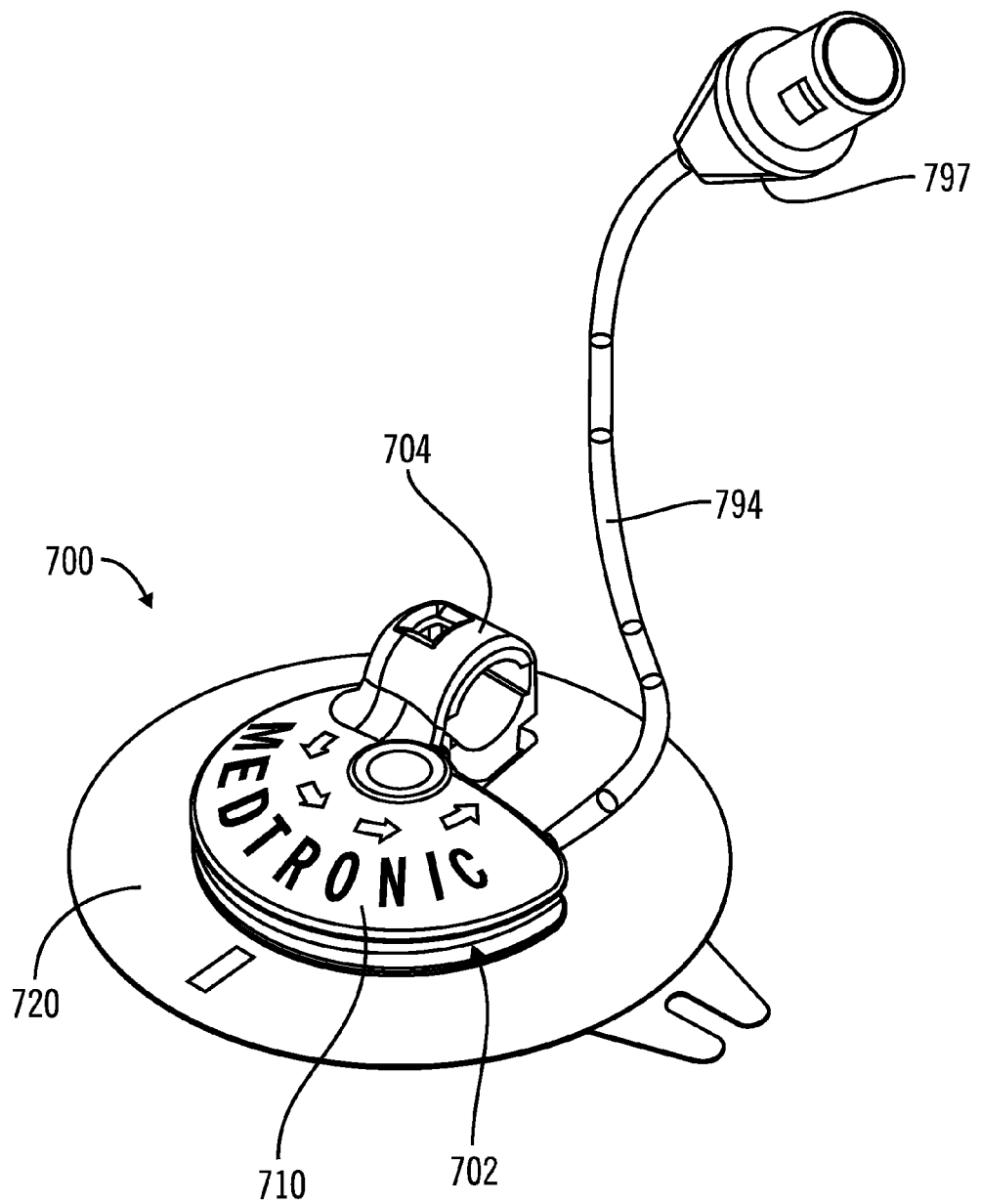

FIGS. 14A & 14B, in which like elements share like reference numbers, are perspective views of one embodiment of an injection device made in accordance with the invention. In this embodiment, the injection device includes a tube with an external device fitting, so that the injection device can be placed in a remote location and attached to an injection pump.

FIG. 14A is a perspective view of the injection device 700 in a stored configuration, the injection device 700 including a body 710 and a patch 720 attached to the body 710. The patch 720 is operable to adhesively attach the injection device 700 to a patient (not shown). The body 710 has a groove 702 around its outer circumference operable to receive tube 794 in the stored configuration. One end of the tube 794 is in fluid communication with an injection port (not shown) of the injection device 700 to deliver a therapeutic agent into the body of a patient. The other end of the tube 794 is in fluid communication with the external device fitting 797, which can be extended to a convenient location when the injection device 700 is in a difficult to access location or which can be connected to an injection pump (not shown). In this example, the body 710 includes a fitting receiver 704 operable to receive and store the external device fitting 797 when the injection device 700 is in the stored configuration with the tube 794 wrapped around the body 710. FIG. 14B is a perspective view of the injection device 700 in a deployed configuration, with the external device fitting 797 uncoupled from the fitting receiver 704 and the tube 794 uncoiled from the groove 702 in the body 710. In operation, the injection device 700 can be placed on a remote location on the body of the patient, such as a remote location not normally accessible for injection by conventional means, and the tube 794 extended to allow convenient connection to an injection pump.

FIGS. 15-20, in which like elements share like reference numbers, are various views of one embodiment of a body for an injection device made in accordance with the invention. The body includes cutouts to provide inspection and ventilation at the attachment point of the injection device to the patient.

The single piece body for an injection device can include a planar deck having a patient face, the planar deck having cutouts around and through the planar deck, the planar deck including a delivery tube port on the patient face; a port segment attached opposite the patient face of the planar deck, the port segment including an introducer port including an introducer channel and an injection port including an injection channel the introducer channel being in fluid communication with the injection channel and the delivery tube port; and attachment projections protruding from the patient face. In one embodiment, the attachment projections are operable for plastic welding.

The single piece body can be used with an injection device for delivering a therapeutic agent to a patient including the single piece body. The injection device further includes a delivery tube for subcutaneous delivery of the therapeutic agent to the patient, the delivery tube projecting from and being generally perpendicular to the patient face, the delivery tube being in fluid communication with the injection port; and a patch, the patch being plastically welded to the attachment projections and being operable to adhesively attach to the patient.

Figure 15:
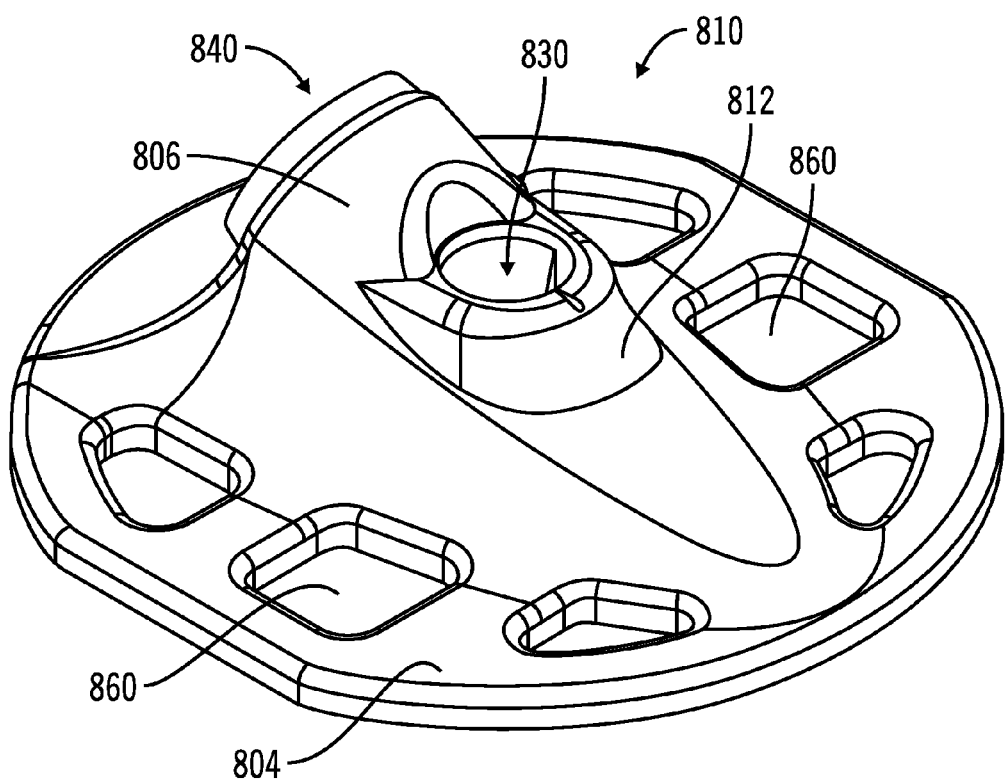
FIGS. 15-20 are front perspective, top side, left side, bottom side, bottom perspective, and detail views, respectively, of one embodiment of a body for an injection device made in accordance with the invention.
Figure 16:
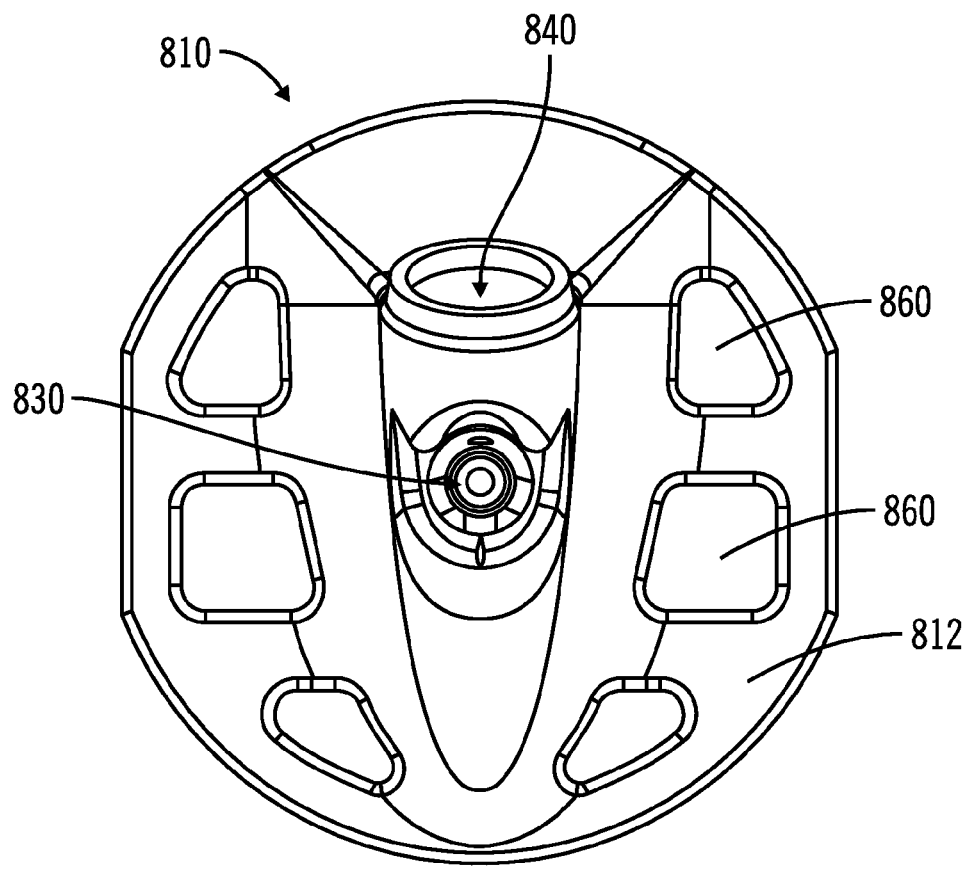

FIGS. 15 & 16 are a front perspective view and a top side view, respectively, of a body 810 including a port face 812. The port face 812 includes an introducer port 830 and an injection port 840. The body 810 has a generally planar deck 804 with cutouts 860 spaced around and passing through the planar deck 804. The body 810 also has a port segment 806 rising above the planar deck 804 and including the introducer port 830 and an injection port 840. The body 810 is a single piece body, which is defined herein as a body formed as a single piece and is not a group of separate pieces assembled to form the body.

Figure 17:
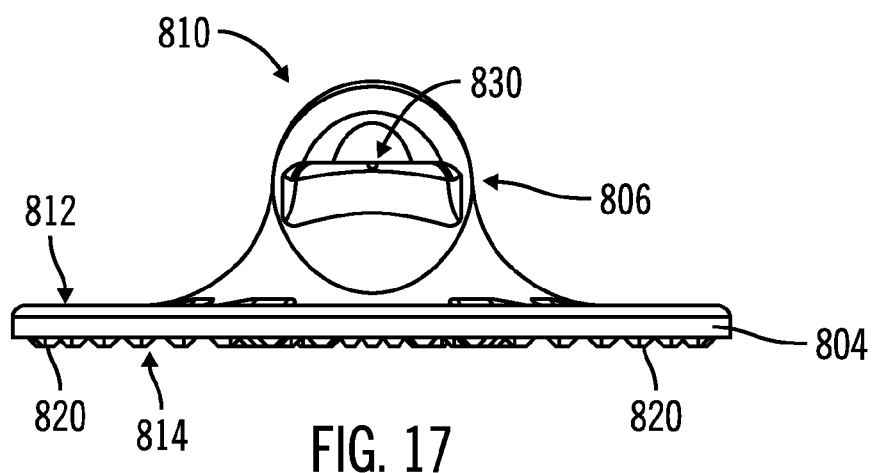

FIG. 17 is a left side view of the body 810. The patient face 814 is opposite the port face 812 on the planar deck 804 and is operable to connect the body 810 to a patch (not shown) to adhesively attach the injection device to a patient. In this embodiment, the patient face 814 of the planar deck 804 includes a number of attachment projections 820 (in this example, the attachment projections 820 being bumps) protruding from the planar deck 804 to allow a patch to be plastically welded to the body 810. Those skilled in the art will appreciate that different attachment projections, such as truncated pyramids, bumps, radial lines, concentric rings, or the like, can be selected as desired for a particular application. In yet another embodiment, the patch can be attached to the body 810 with an adhesive.

Figure 18:
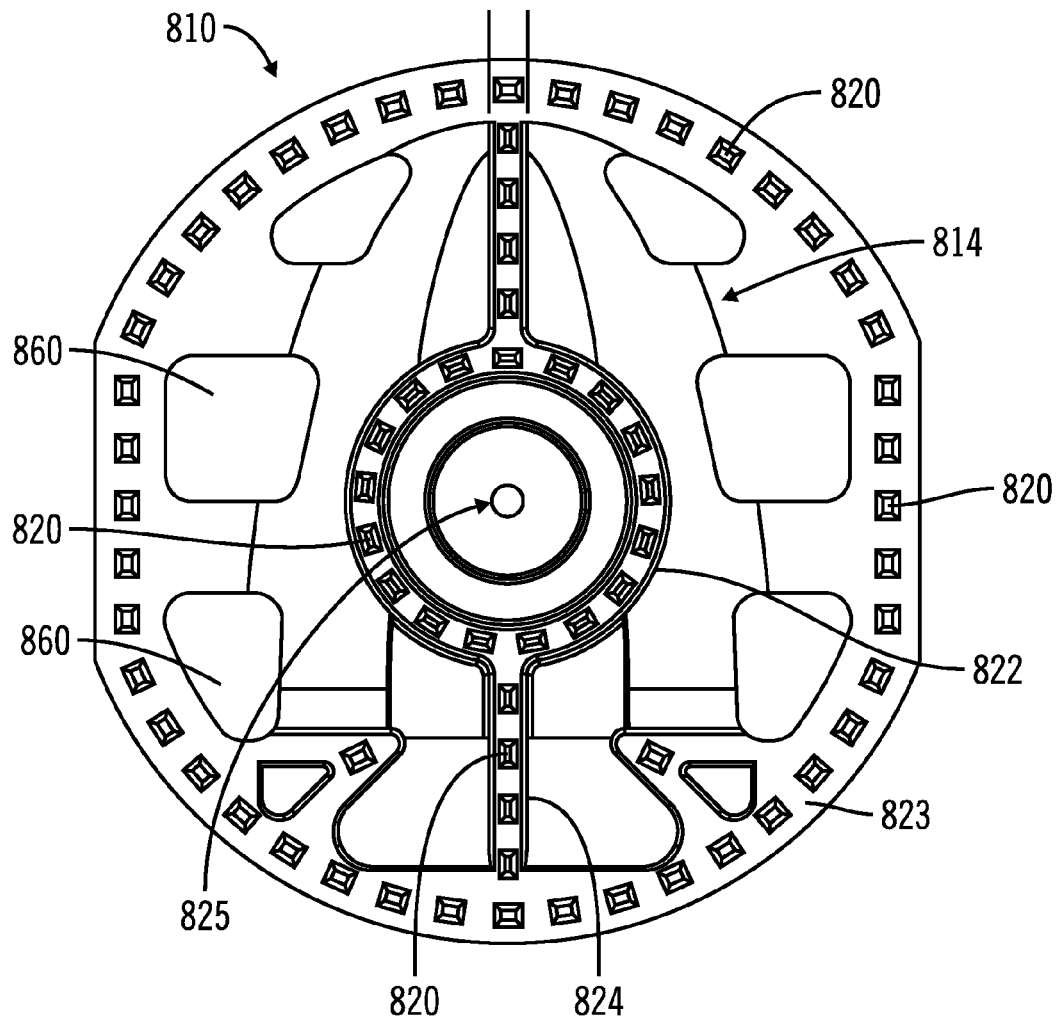
Figure 19:
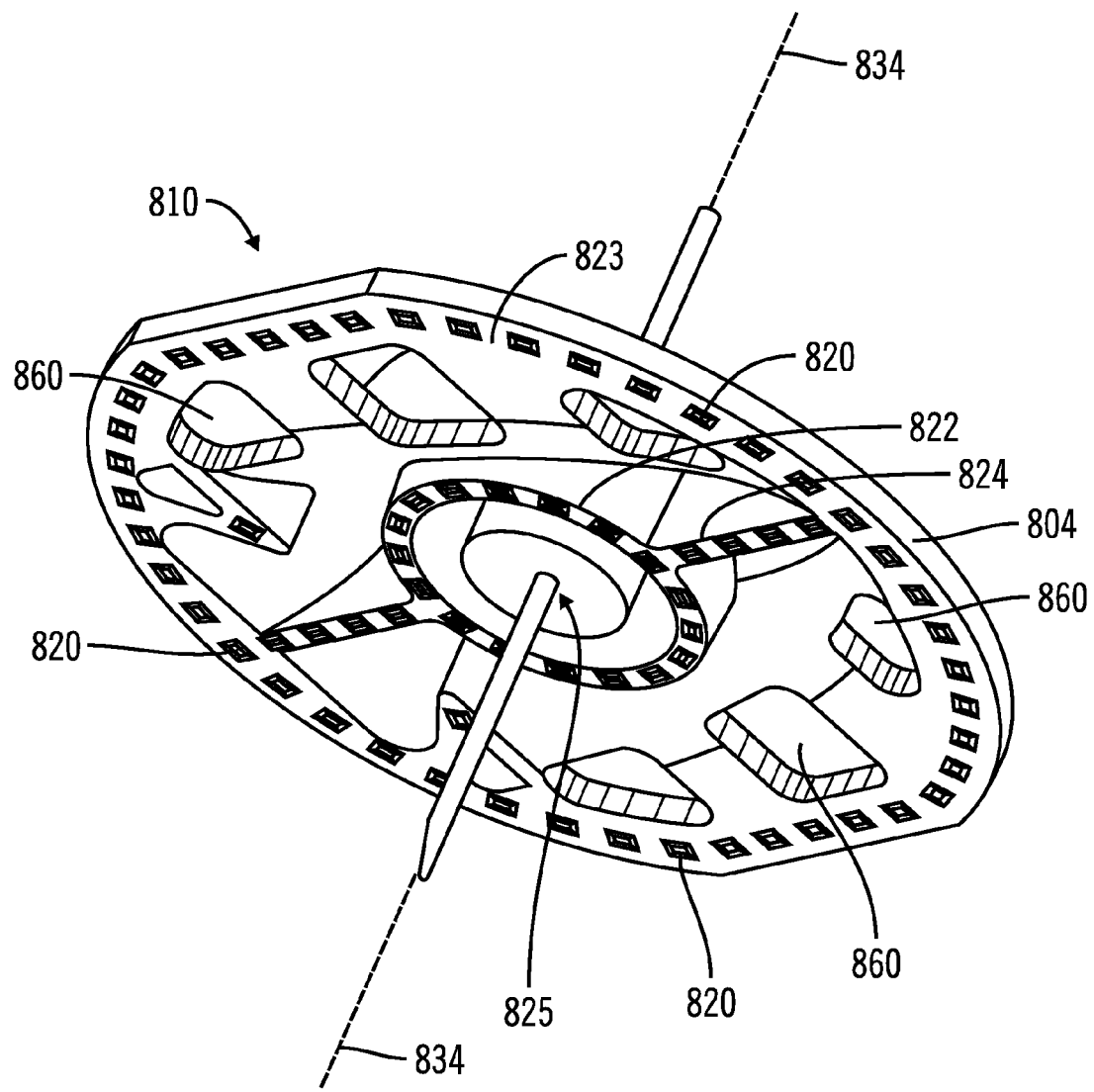

FIGS. 18 & 19 are a bottom side view and a bottom perspective view, respectively, of the body 810. The attachment projections 820 are arranged around the outer circumference 823 of the patient face 814, around an inner circle 822 about a delivery tube port 825 on the introducer axis 834, and along diameter segments 824 between the outer circumference 823 and the inner circle 822 which follow the length of the port segment. In this example, the attachment projections 820 are truncated pyramids.

Figure 20:
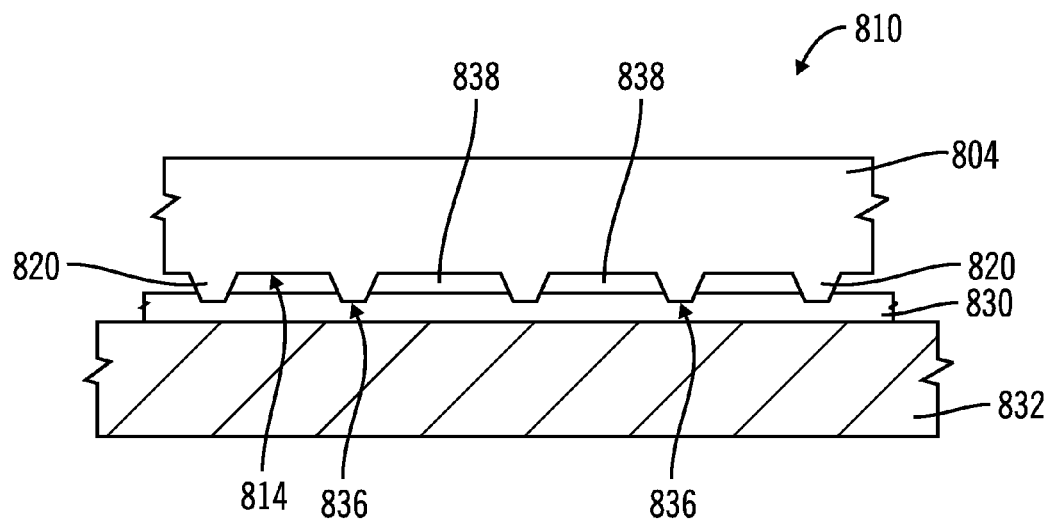

FIG. 20 is a section view of the planar deck 804 of the body 810 along the outer circumference through the attachment projections 820. In this example, the body 810 is plastically welded to a patch 830, which is attached to the skin 832 of a patient. The attachment projections 820 are deformed from the truncated pyramid to a flattened, rounded shape from welding the attachment projections 820 to the patch 830 at each fixation point 836. In this example, the tips of the attachment projections 820 are welded into the patch 830, i.e., the tips of the attachment projections rest below the surface of the patch at the fixation points 836 where the attachment projections 820 join the patch 830. In cross section through adjacent attachment projections 820, the patient face 814 and the patch 830 define a ventilation gap 838 to provide ventilation and air circulation between the planar deck 804 and the patch 830, cooling the skin 832 across the patch 830 from the ventilation gap 838.

Those skilled in the art will appreciate that the design of the patch 830 can be selected as desired for a particular application. The patch can be made of any biocompatible material with biocompatible adhesive operable to hold the weight of the injection device to the skin for a predetermined number of days. The patch design also needs to account for ventilation and circulation between the patch and the skin. In one example, the patch is a continuous sheet of adhesive material. In another example, the patch is a mesh sheet of adhesive material including perforations. In yet another example, the patch is a continuous sheet of adhesive material with holes cut into the continuous sheet. The holes can align with features of the body of the injection device, such as the cutouts, as desired. The holes can optionally be the same size as the cutouts. In yet another example, the patch is a continuous sheet of adhesive material with holes cut into the continuous sheet, and mesh applied across the holes. In yet another example, the patch can be made of a transparent material to allow the condition of the skin around and below the injection device to be monitored. In one example, adhesive patches are constructed of pressure sensitive acrylic-based adhesives with non-woven polyester backings.

Those skilled in the art will further appreciate that the design of the body of the injection device can be selected as desired for a particular application. In one example, the number and position of the cutouts in the planar deck can be selected to provide ventilation to the skin while maintaining sufficient rigidity for the planar deck. In another example, the number and position of the cutouts can be selected to allow observation of the condition of the skin around and below the injection device. In yet another example, the body of the injection device can be made of a transparent material to allow the condition of the skin around and below the injection device to be monitored. This is particularly useful when the patch includes holes or is made from a transparent material. Exemplary materials for the body of the injection device include polycarbonate, acrylic, or the like. In one embodiment, one or more optical elements can be molded into the body of the injection device to magnify the area or areas of interest.

FIGS. 21-24 are various embodiments of septums for use in an injection device. The septums can be disposed in the injection device channels. In one embodiment, the septum is self sealing to block fluid flow through the septum after a needle has been put through the septum then removed, preventing fluid flow through the port connected to the channel.

Figure 21:
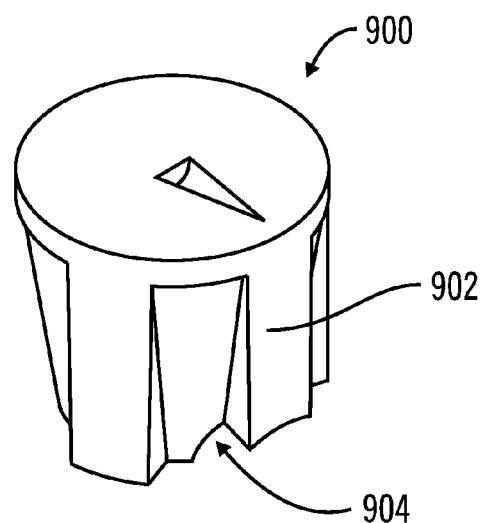
FIG. 21 is a perspective view of one embodiment of an introducer septum for use in an injection device made in accordance with the invention.

FIG. 21 is a perspective view of one embodiment of an introducer septum for use in an injection device made in accordance with the invention. In this embodiment, the introducer septum is irregular-shaped, i.e., the introducer septum has an irregular shape. The introducer septum 900 includes a number of legs 902 to secure the introducer septum 900 in the introducer channel.

Figure 22:
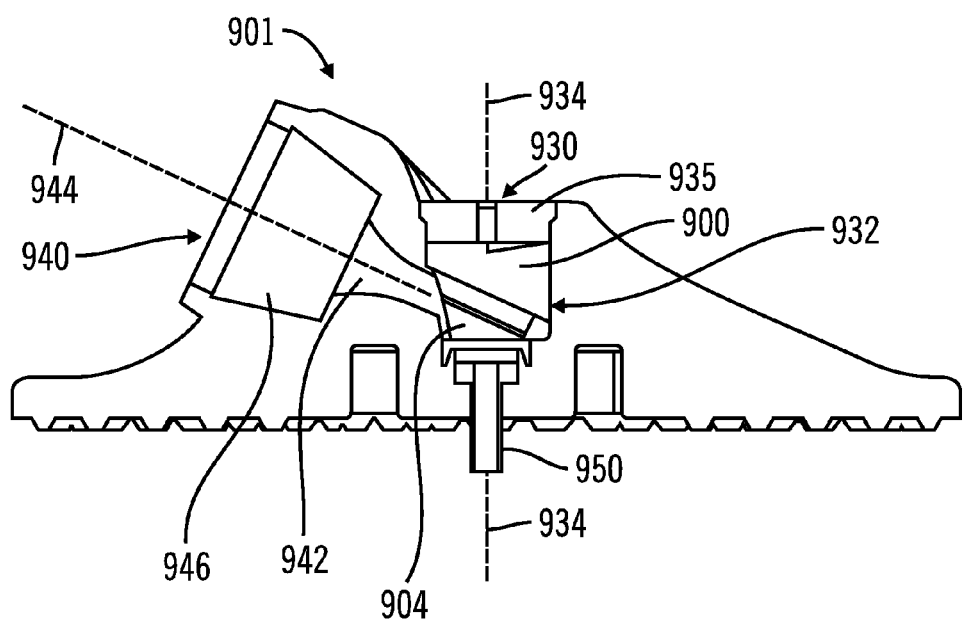
FIG. 22 is a section view of an injection device made in accordance with the invention including the introducer septum of FIG. 21.

FIG. 22 is a section view of an injection device made in accordance with the invention including the introducer septum of FIG. 20. The section bisects the introducer port 930 and the injection port 940, and includes the introducer axis 934 and injection axis 944. The delivery tube 950 is operably connected to the introducer port 930 and defines an introducer axis 934, the delivery tube 950 being in fluid communication with the injection port 940. The introducer port 930 includes an introducer channel 932, with an introducer port cover 935 and the introducer septum 900 disposed in the introducer channel 932. The introducer septum 900 is secured in the introducer channel 932 of the injection device 901 by legs 902. The injection port 940 includes an injection channel 942 defining an injection axis 944 with an injection septum 946 disposed in the injection channel 942. The injection channel 942 is in fluid communication with the delivery tube 950 through a septum connection channel 904 in the introducer septum 900. The introducer septum 900 both connects the injection port 940 to the delivery tube 950 and fills extra space within the introducer channel 932 to avoid an unnecessary amount of therapeutic agent from collecting in the introducer channel 932.

Figure 23:
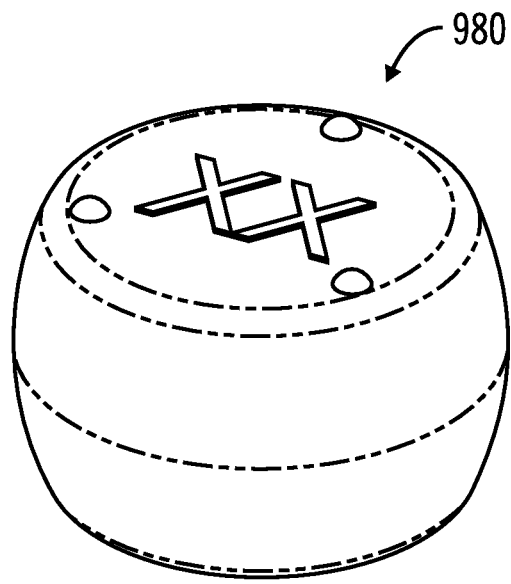
FIG. 23 is a perspective view of one embodiment of a septum for use in an injection device made in accordance with the invention.

FIG. 23 is a perspective view of one embodiment of a septum for use in an injection device made in accordance with the invention. In this embodiment, the septum is barrel-shaped. The barrel-shape septum 980 can be used as an introducer septum or an injection septum as desired for a particular application.

Figure 24A:
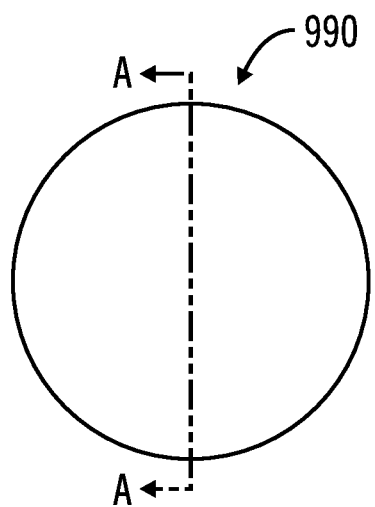
FIGS. 24A & 24B are top side and section views, respectively, of one embodiment of a septum for use in an injection device made in accordance with the invention.
Figure 24B:
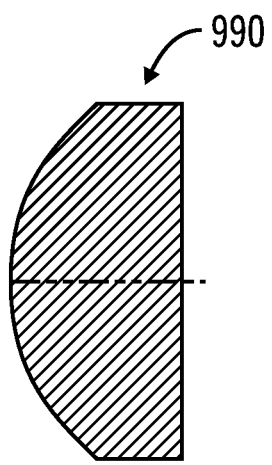

FIGS. 24A & 24B are top side and A-A section views, respectively, of one embodiment of a septum for use in an injection device made in accordance with the invention. In this embodiment, the septum is dome-shaped. The dome septum 990 can be used as an introducer septum or an injection septum as desired for a particular application.

FIGS. 25-30 illustrate an on-body injector for use with an injection device made in accordance with the invention. Referring to FIG. 5B, an on-body injector 192 is mateable with the injection port 140 of the injection device 100 and can be used to deliver a therapeutic agent through the injection port 140. The on-body injector 192 can include a reservoir to hold the therapeutic agent. In one embodiment, the on-body injector 192 can deliver a basal and/or bolus dose of the therapeutic agent.

Figure 25:
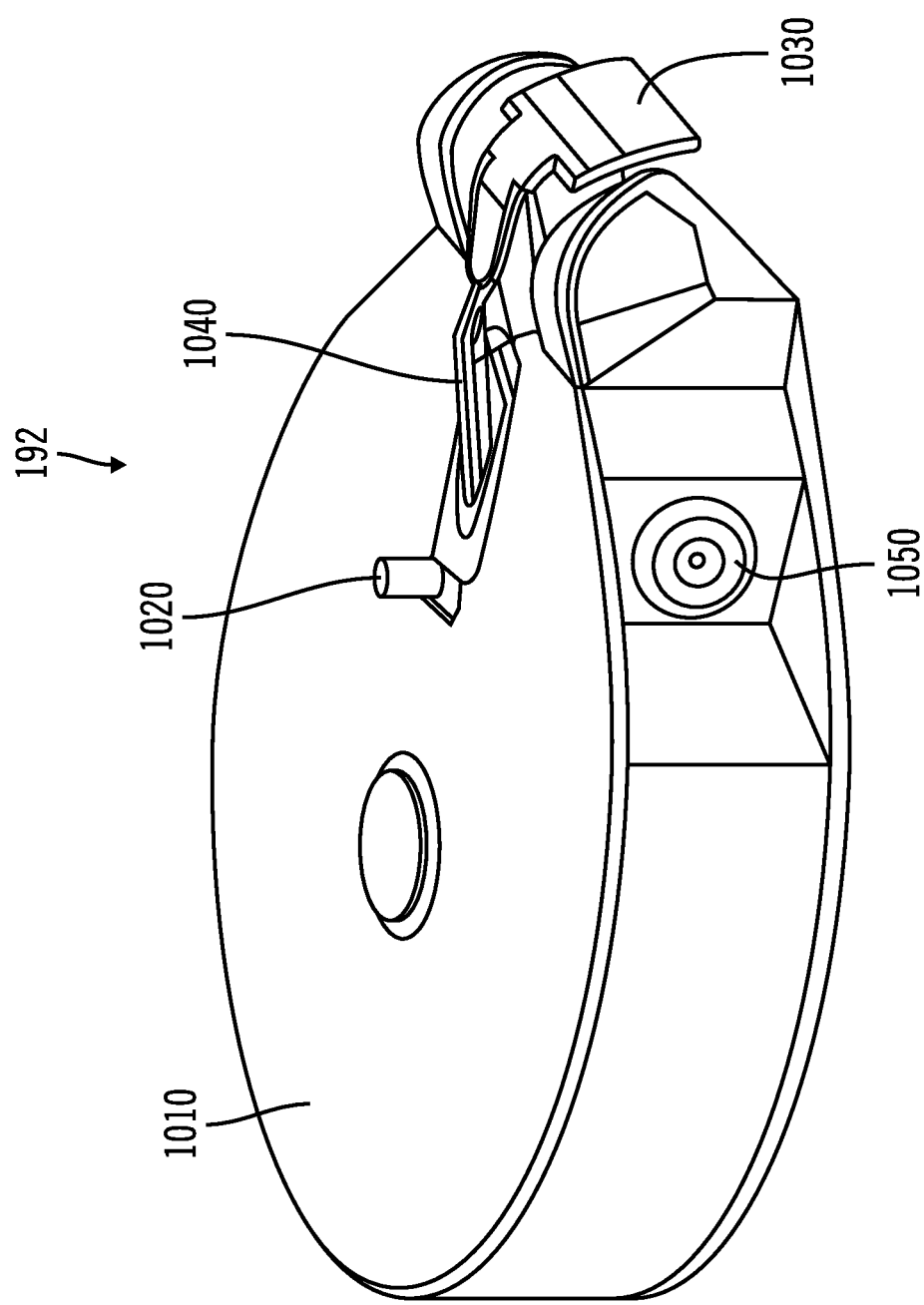
FIG. 25 is a perspective view of one embodiment of an on-body injector for use with an injection device made in accordance with the invention.

FIG. 25 is a perspective view of one embodiment of an on-body injector for use with an injection device made in accordance with the invention. The on-body injector 192 includes a housing 1010 to contain the internal components of the on-body injector, a lock 1020 to secure the on-body injector 192 to the injection device, and a fill port 1050 for filling or refilling the on-body injector 192 with a therapeutic agent for bolus and/or basal injection.

The on-body injector 192 also includes a button 1030 which can be used to administer a bolus injection. A gap in the bolus injection flow path prevents bolus injection unless the button 1030 is depressed. The button 1030 is operably connected to the bolus injection needle 1040 to slide the bolus injection needle 1040 along the injection axis. When the button 1030 is depressed, the button 1030 advances the bolus injection needle tip to close a gap between the bolus injection needle tip and the injection port of the injection device and to form an injection flow path to deliver a bolus injection to the patient. The button 1030 also advances a plunger through the bolus reservoir to deliver a predetermined bolus volume to the patient through the injection flow path once the gap is closed and the injection flow path is complete. Those skilled in the art will appreciate that the button 1030 as defined herein can be any mechanism or combination of mechanisms operable to advance the bolus injection needle through the gap and deliver the bolus injection. In one example, the button slides in a track or similar guiding geometry. In another example, the button is a lever that moves the bolus injection needle and plunger. Those skilled in the art will appreciate that the button can be activated by secondary devices, such as solenoids, motors, pneumatic activators, or the like.

Figure 26:
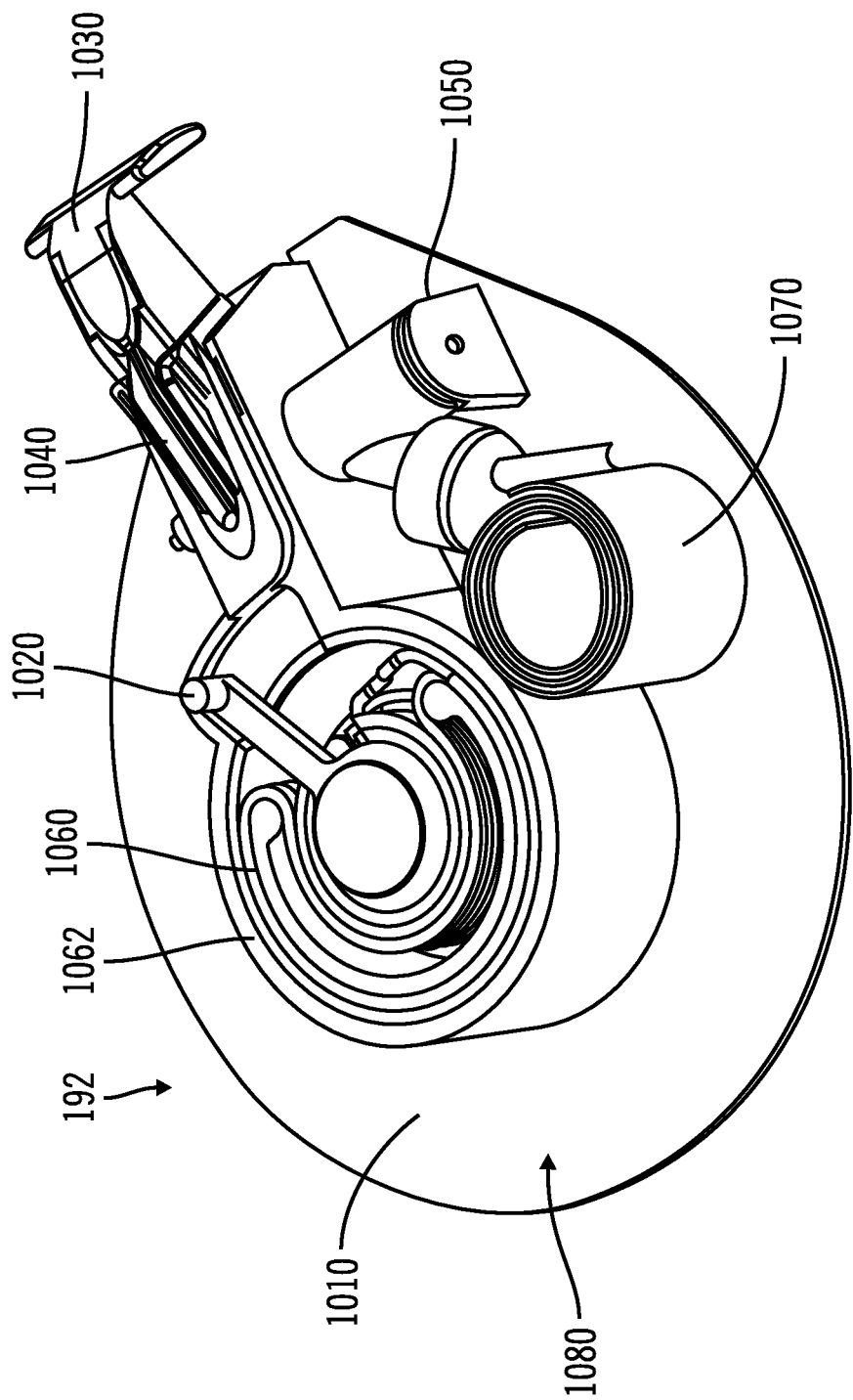
FIG. 26 is a partial perspective view of portions of one embodiment of an on-body injector for use with an injection device made in accordance with the invention.

FIG. 26, in which like elements share like reference numbers with FIG. 25, is a partial perspective view of portions of one embodiment of an on-body injector for use with an injection device made in accordance with the invention. In FIG. 26, the top portion of the housing 1010 has been removed to reveal the interior components. In this embodiment, basal injection is provided by a pressurized reservoir 1070, which is at least partially filled with a therapeutic agent. The pressurized reservoir 1070 in this example is a spring coil that at least partially uncoils within an interior track 1080 within the housing 1010 when the pressurized reservoir 1070 is pressurized, i.e., when the pressurized reservoir is at least partially filled with a therapeutic agent. The pressurized reservoir 1070 can be filled through the fill port 1050. For basal injection, the therapeutic agent is delivered through the introducer port of the injection device, which is in fluid communication with the delivery tube of the injection device. The therapeutic agent passes from the pressurized reservoir 1070, through the flow restrictor 1060, and into the patient through the injection device. The flow restrictor 1060 in this example is tubing having a length and interior diameter selected to provide a desired pressure drop, supported by tubing support structure 1062. Those skilled in the art will appreciate that the flow restrictor can be any device providing a pressure drop between the pressurized reservoir and the delivery tube as desired for a particular application. In another example, the flow restrictor can be an orifice. In another example, the flow restrictor can be a bypass channel that re-directs access to medication. In one embodiment, the flow restrictor can be selected to provide a predetermined basal flow rate, such as a basal flow rate of 20 units of insulin per 24 hours, 30 units of insulin per 24 hours, or 40 units of insulin per 24 hours. Those skilled in the art will further appreciate that the pressurized reservoir can be any device pressurizing the therapeutic agent as desired for a particular application. In other examples, the pressurized reservoir can be an elastic bladder, a spring-loaded inelastic bladder, a fluid (gas or liquid) pressurized bladder, or the like.

Figure 27:
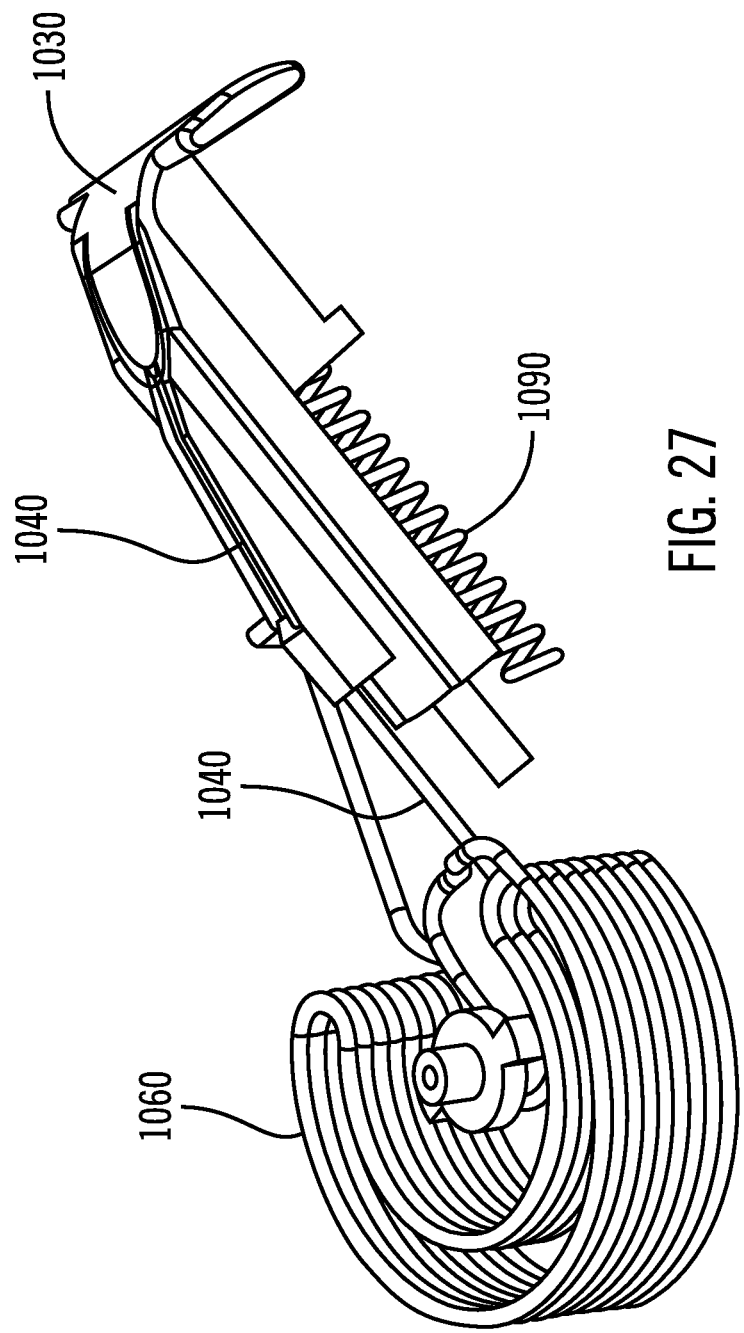
FIG. 27 is a partial perspective view of portions of one embodiment of an on-body injector for use with an injection device made in accordance with the invention.

FIG. 27, in which like elements share like reference numbers with FIGS. 25 & 26, is a partial perspective view of portions of one embodiment of an on-body injector for use with an injection device made in accordance with the invention. A button spring 1090 provides a bias force to the button 1030, to bias the bolus injection needle 1040 away from the injection port of the injection device and provide the gap between the bolus injection needle tip and the injection port when the button is not depressed.

Figure 28:
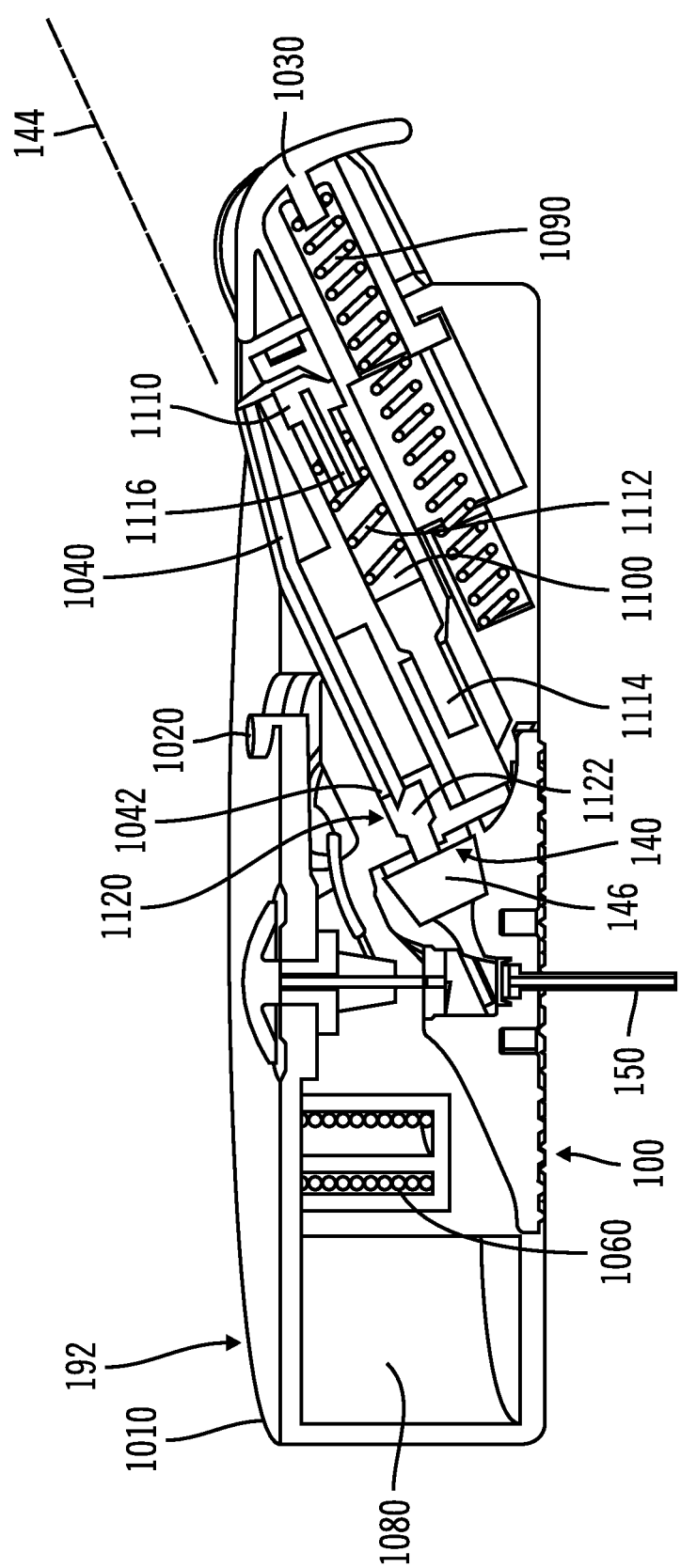
FIG. 28 is a section view of one embodiment of an injection device and on-body injector for use with an injection device made in accordance with the invention.

FIG. 28, in which like elements share like reference numbers with FIGS. 25-27, is a section view of one embodiment of an injection device and on-body injector for use with an injection device made in accordance with the invention. FIG. 28 illustrates the cross-section of the on-body injector 192 and the injection device 100 divided along the bolus injection needle 1040.

The bolus injection needle tip 1042 is aligned with the injection septum 146 of the injection port 140 along the injection axis 144. The button spring 1090 biases the bolus injection needle tip 1042 away from the injection septum 146 to create a gap 1120 between the bolus injection needle tip 1042 and the injection port 140 when the button 1030 is not depressed. When the button 1030 is depressed, the bolus injection needle 1040 slides along the injection axis 144, closing the gap 1120 and inserting the bolus injection needle tip 1042 through the injection septum 146. In this example, the bolus injection needle tip 1042 also passes through a needle tip septum 1122. Once the bolus injection needle tip 1042 has passed through the injection septum 146, and injection flow path for bolus injection is formed from the bolus reservoir 1100, through the bolus injection needle 1040, through the delivery tube 150, and into the patient. When the button 1030 is released, the bolus injection needle 1040 slides back to the initial position and the gap 1120 is restored. The bolus injection needle tip 1042 is always embedded within a septum (the needle tip septum 1122 or the injection septum 146) to keep the bolus injection needle tip 1042 clean, and to keep the bolus injection needle tip 1042 capped so no therapeutic agent will leak out of the bolus injection needle tip 1042.

The on-body injector 192 includes a bolus reservoir 1100 with a plunger 1110 slideably disposed within the bolus reservoir 1100 and a bolus stop 1114 fixed at one end of the bolus reservoir 1100. A bolus spring 1112 biases the plunger 1110 away from the bolus stop 1114. The plunger 1110 is coupled to the button 1030 so that the plunger 1110 slides through the bolus reservoir 1100 when the button 1030 is depressed. The plunger 1110 includes a central passage 1116 to allow fluid from the bolus reservoir 1100 to flow through the plunger 1110 into the bolus injection needle 1040 and to the patient through the bolus injection needle 1040. The volume of the bolus reservoir 1100 can be selected to provide a predetermined bolus volume to the patient. In one embodiment, the predetermined bolus volume is 2 units of insulin.

When the plunger 1110 reaches a final position at the end of the bolus reservoir 1100 and contacts the bolus stop 1114, the bolus stop 1114 blocks the central passage 1116 in the plunger 1110. Thus, the plunger 1110 blocks the injection flow path after the predetermined bolus volume has been delivered. This prevents additional undesired delivery of a therapeutic agent should the injection flow path remains in place from a failure, such as the bolus injection needle 1040 becoming stuck in the injection port 140 of the injection device 100, a failure of the button 1030 or related mechanism, or the like.

Figure 29:
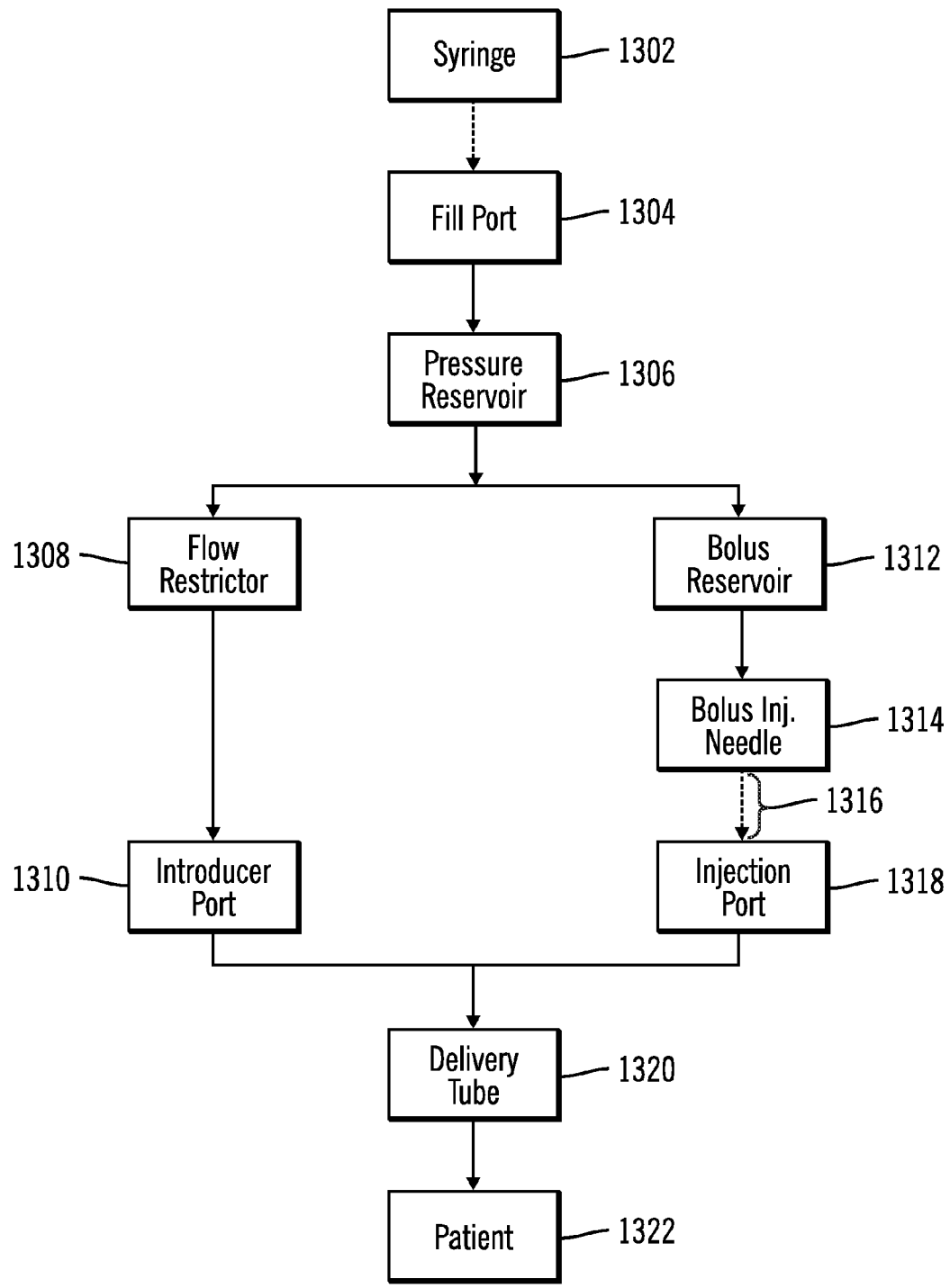
FIG. 29 is a block diagram of one embodiment of an injection device and on-body injector made in accordance with the invention.

FIG. 29 is a block diagram of one embodiment of an injection device and on-body injector made in accordance with the invention. FIG. 29 illustrates the flow paths through the injection device and on-body injector, which can be used for a bolus injection and/or a basal injection.

Both the bolus injection and basal injection flow paths include an optional syringe 1302, an optional fill port 1304, a pressure reservoir 1306, a delivery tube 1320, supplying the patient 1322. The basal injection flow path also includes a flow restrictor 1308 and an introducer port 1310 between the pressure reservoir 1306 and the delivery tube 1320. The bolus injection flow path also includes a bolus reservoir 1312, a bolus injection needle 1314, a gap 1316, an injection port 1318 between the pressure reservoir 1306 and the delivery tube 1320.

The optional syringe 1302 can be inserted in the optional fill port 1304 to fill or refill the pressure reservoir 1306. As illustrated by the dashed line between the optional syringe 1302 and the optional fill port 1304, the optional syringe 1302 is not permanently attached to the optional fill port 1304 and can be removed. In one embodiment, the pressure reservoir 1306 can be pre-filled with a therapeutic agent when the on-body injector is delivered to the patient, so that the fill port 1304 is used for refilling the pressure reservoir 1306. In another embodiment, the pressure reservoir 1306 is empty when the on-body injector is delivered to the patient, so that the fill port 1304 is used for initially filling the pressure reservoir 1306. In yet another embodiment, the optional fill port 1304 is omitted and the on-body injector is a single use device with the pressure reservoir 1306 pre-filled with a therapeutic agent. Those skilled in the art will appreciate that the optional syringe 1302 can be any device operable to deliver a therapeutic agent into the fill port 1304 as desired for a particular application.

For basal injection, the pressure reservoir 1306 of the on-body injector provides the therapeutic agent through the flow restrictor 1308 of the on-body injector to the introducer port 1310 of the injection device. The delivery tube 1320 of the injection device applies the therapeutic agent to the patient 1322. The flow restrictor 1308 can be any device providing a pressure drop between the pressurized reservoir and the delivery tube as desired for a particular application. In one example, the flow restrictor can be tubing having a length and interior diameter selected to provide a desired pressure drop. In another example, the flow restrictor can be an orifice. In another example, the flow restrictor can be a bypass channel that re-directs access to medication. In one embodiment, the flow restrictor can be selected to provide a predetermined basal flow rate, such as a basal flow rate of 20 units of insulin per 24 hours, 30 units of insulin per 24 hours, or 40 units of insulin per 24 hours.

For bolus injection, the pressure reservoir 1306 of the on-body injector fills the bolus reservoir 1312 of the on-body injector with therapeutic agent. The on-body injector delivers a predetermined bolus volume (the volume of the pressure reservoir 1306) when the patient depresses a button. When the button is depressed, the tip of the bolus injection needle 1314 closes the gap 1316 between the bolus injection needle 1314 of the on-body injector and enters the injection port 1318 of the injection device to complete the bolus injection flow path. The gap 1316 as illustrated by the dashed lines between the bolus injection needle 1314 of the on-body injector and the injection port 1318 of the injection device is present when the button is not depressed to prevent bolus injection unless the button is depressed. Depressing the button also delivers the therapeutic agent from the bolus reservoir 1312, through the bolus injection needle 1314, through the injection port 1318, through the delivery tube 1320, and into the patient 1322. In one embodiment, the predetermined bolus volume is 2 units of insulin. The bolus injection flow path can optionally include a flow blocker (such as the bolus stop 1114 of FIG. 28, for example) which blocks the bolus injection flow path after the predetermined bolus volume has been delivered.

Referring to FIG. 29, for one embodiment of an on-body injector for a bolus injection, the injection device has an injection port 1318 in fluid communication with a delivery tube 1320 with the injection port 1318 lying on an injection axis. The on-body injector includes a bolus reservoir 1312; a bolus injection needle 1314 in fluid communication with the bolus reservoir 1312, the bolus injection needle 1314 having a bolus injection needle tip aligned with the injection port 1318, the bolus injection needle 1314 being slideably biased away from the injection port to define a gap 1316 between the bolus injection needle tip and the injection port 1318; and a button operably connected to the bolus injection needle 1314 to slide the bolus injection needle 1314 along the injection axis. The button is operable to advance the bolus injection needle tip to close the gap 1316 and advance the bolus injection needle tip into the injection port 1318 to form an injection flow path from the bolus reservoir 1312, through the bolus injection needle 1314, through the delivery tube 1320, and into the patient 1322. The button is further operable to advance a plunger through the bolus reservoir 1312 to deliver a predetermined bolus volume to the patient 1322 through the injection flow path.

For one embodiment of an on-body injector for a basal injection, the injection device has an introducer port 1310 in fluid communication with a delivery tube 1320. The on-body injector includes a pressurized reservoir 1306; a flow restrictor 1308 disposed between the pressurized reservoir 1306 and the delivery tube 1320, the flow restrictor 1308 being tubing having a length and interior diameter selected to provide a desired pressure drop; and a fill port 1304 in fluid communication with the pressurized reservoir.

Figure 30:
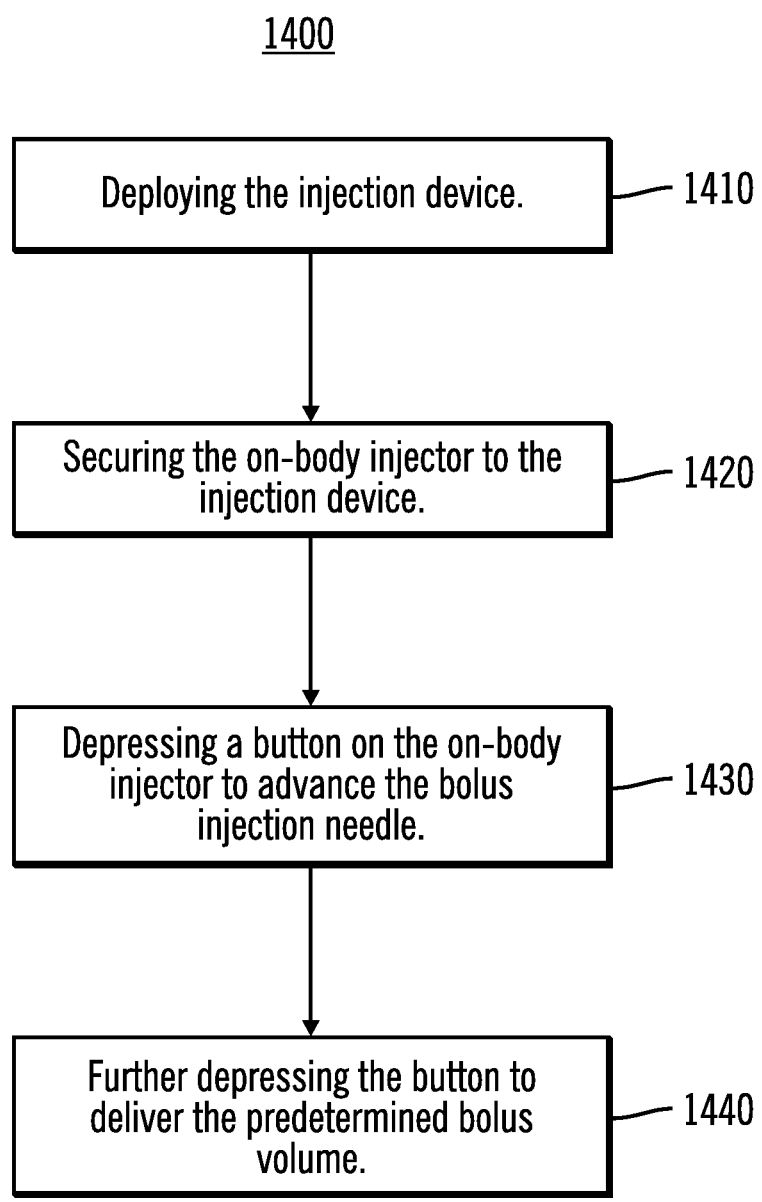
FIG. 30 is a flow chart of a method of use for an on-body injector in accordance with the invention.

FIG. 30 is a flow chart of a method of use for an on-body injector in accordance with the invention. The method 1400 is a method of use for an on-body injector with an injection device for delivering a predetermined bolus volume to a patient. The method 1400 includes deploying the injection device 1410 in the patient, the injection device having a delivery tube placed in the patient and an injection port in fluid communication with the delivery tube; securing the on-body injector to the injection device 1420, the on-body injector having a bolus injection needle aligned with and spaced apart from the injection port; depressing a button on the on-body injector to advance the bolus injection needle 1430 into the injection port; and further depressing the button to deliver the predetermined bolus volume 1440 from the on-body injector through the bolus injection needle, through the delivery tube, and into the patient. The method 1400 can further include releasing the button to retract the bolus injection needle from the injection port.

The method 1400 can also include delivering a basal injection. In this embodiment, the injection device further includes an introducer port in fluid communication with the delivery tube, and the on-body injector further includes a pressurized reservoir in fluid communication with a basal injection needle inserted in the introducer port. The method 1400 further includes delivering a basal injection from the pressurized reservoir through the basal injection needle, through the delivery tube, and into the patient. the on-body injector can further include a fill port in fluid communication with the pressurized reservoir, in which case the method 1400 can further include delivering a therapeutic agent thorough the fill port into the pressurized reservoir.

FIGS. 31-38 illustrate an electronic injector for use with an injection device or for independent use. The electronic injector uses a Micro-Electro-Mechanical System (MEMS) pump to deliver a therapeutic agent from a reservoir to a patient.

Figure 31:
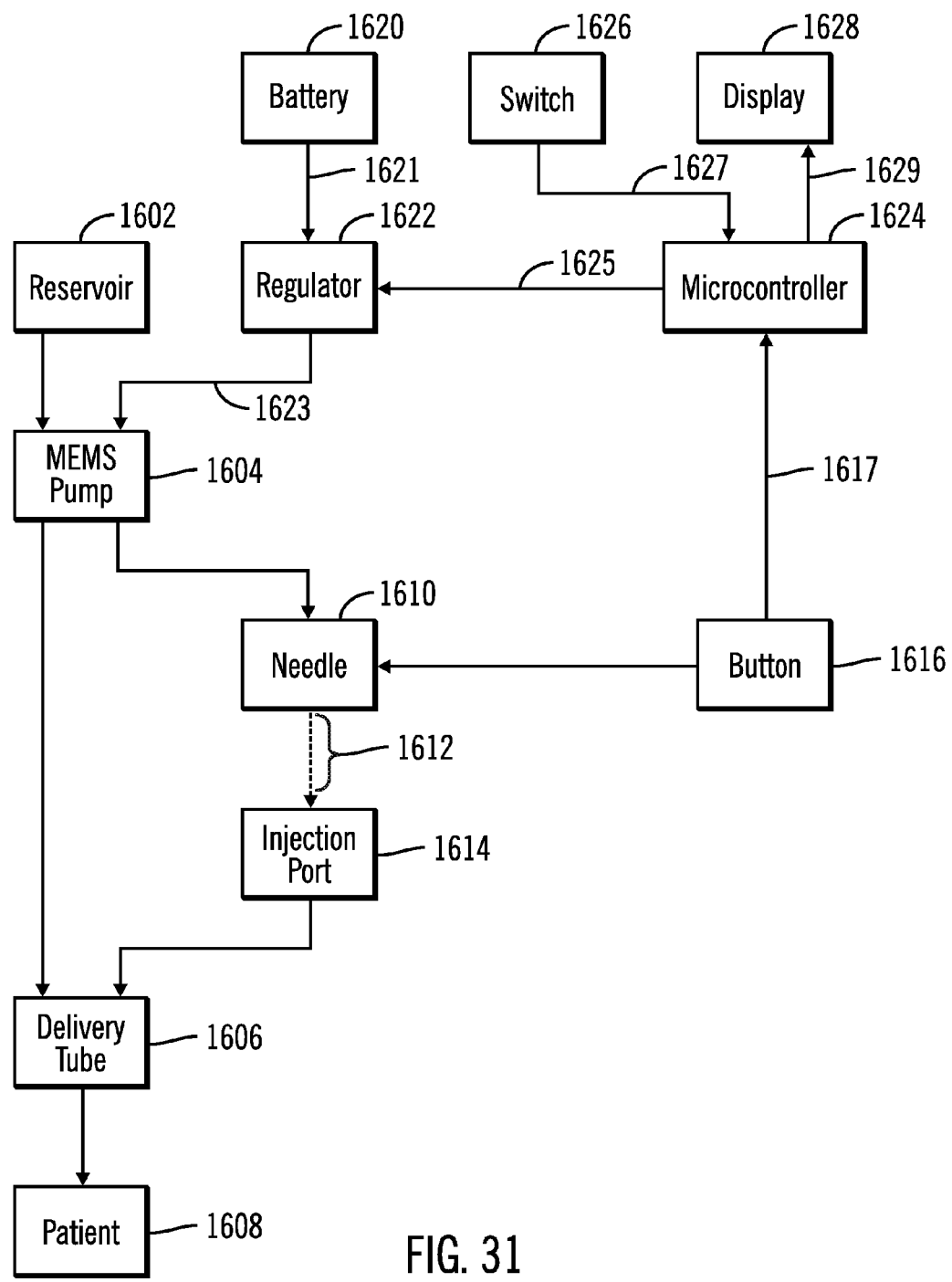
FIG. 31 is a block diagram of one embodiment of an injection device and electronic on-body injector made in accordance with the invention.

FIG. 31 is a block diagram of one embodiment of an injection device and electronic on-body injector made in accordance with the invention. FIG. 31 illustrates the flow paths through and electrical signals for the injection device and electronic on-body injector, which can be used for a bolus injection and/or a basal injection. The injection device is deployed in the patient with a delivery tube placed subcutaneously and the electronic on-body injector is secured to the injection device.

The basal injection flow path includes a fluid reservoir 1602, a MEMS pump 1604, and a delivery tube 1606 supplying the patient 1608. The bolus injection flow path includes the fluid reservoir 1602, the MEMS pump 1604, a bolus injection needle 1610, a gap 1612, an injection port 1614, and the delivery tube 1606 supplying the patient 1608. The bolus injection mechanism also includes a bolus needle button 1616 operable to advance the bolus injection needle 1610 and to activate the MEMS pump 1604 to deliver a predetermined bolus volume.

The electronic portion of the electronic on-body injector includes a battery 1620, a regulator 1622, and a microcontroller 1624. The battery 1620 has a DC power output 1621 which is provided to the regulator 1622. The battery 1620 is also operably connected (not shown) to provide power to the microcontroller 1624. The regulator 1622 is operably connected to the battery 1620 to convert the DC power output 1621 to a pump drive signal 1623 in response to a regulator control signal 1625 from the microcontroller 1624. The regulator 1622 provides the pump drive signal 1623 to the MEMS pump 1604. The pump drive signal 1623 can be a basal pump drive signal or a bolus pump drive signal as required. The MEMS pump 1604 is responsive to the pump drive signal 1623 to control flow of the fluid from the fluid reservoir 1602, through the MEMS pump 1604, through the delivery tube 1606, and into the patient 1608.

The microcontroller 1624 controls the electronic on-body injector. The microcontroller 1624 receives a bolus needle button signal 1617 from the bolus needle button 1616, which activates MEMS pump 1604 to deliver a predetermined bolus volume to the patient through the bolus injection flow path. The microcontroller 1624 provides the regulator control signal 1625 to the regulator 1622, controlling the pump drive signal 1623. The microcontroller 1624 can also optionally be responsive to a control switch signal 1627 from a control switch 1626 and/or can provide a display signal 1629 to a display 1628. The control switch 1626 and the display 1628 can be used to provide input and output, respectively, to the electronic on-body injector. For example, the display 1628 can be used to display injection options, such as the basal injection rate, and control switch 1626 can be used to select one of the injection options. The microcontroller 1624 can also include or be associated with memory to store data and/or instructions. The microcontroller 1624 can also be operably connected to one or more sensors to monitor the patient 1608 and/or a wireless interface to communicate with one or more external sensors monitoring the patient 1608 or external communication and/or control systems, such as the internet, a continuous glucose monitoring system, a mobile device, or the like. Exemplary uses for a wireless interface providing communication between the electronic injector and an external system/device include calculating/setting dosages, tracking injection times and volumes, and/or sending reminders to a paired device (computer, phone, tablet, mobile device, or the like).

For basal injection, the fluid reservoir 1602 of the on-body injector provides the therapeutic agent to the patient 1608 through the basal injection flow path (the fluid reservoir 1602, MEMS pump 1604, and delivery tube 1606). In one embodiment, the patient 1608 initiates the basal injection by pressing the control switch 1626, which provides the control switch signal 1627 to the microcontroller 1624, which provides the regulator control signal 1625 to the regulator 1622. In this case, the regulator control signal 1625 is a basal regulator control signal and the regulator 1622 generates the pump drive signal 1623 as a basal pump drive signal. The MEMS pump 1604 delivers the desired basal injection to the patient 1608 in response to the basal pump drive signal. In another embodiment, the patient 1608 selects a desired basal flow rate using the control switch 1626 and the display 1628 before initiating the basal injection. Exemplary basal flow rates can include 20 units of insulin per 24 hours, 30 units of insulin per 24 hours, 40 units of insulin per 24 hours, or the like.

For bolus injection, the fluid reservoir 1602 of the on-body injector provides the therapeutic agent to the patient 1608 through the bolus injection flow path (the fluid reservoir 1602, MEMS pump 1604, bolus injection needle 1610, gap 1612, injection port 1614, and delivery tube 1606). The on-body injector delivers a predetermined bolus volume when the patient depresses the bolus needle button 1616 by activating the MEMS pump 1604 at a predetermined flow rate for a predetermined duration. When the bolus needle button 1616 is depressed, the tip of the bolus injection needle 1610 closes the gap 1612 between the bolus injection needle 1610 of the on-body injector and enters the injection port 1614 of the injection device to complete the bolus injection flow path. The gap 1612 as illustrated by the dashed lines between the bolus injection needle 1610 of the on-body injector and the injection port 1614 of the injection device is present when the bolus needle button 1616 is not depressed to prevent bolus injection unless the bolus needle button 1616 is depressed. Depressing the bolus needle button 1616 also delivers the bolus needle button signal 1617 to the microcontroller 1624, which provides the regulator control signal 1625 to the regulator 1622. In this case, the regulator control signal 1625 is a bolus regulator control signal and the regulator 1622 generates the pump drive signal 1623 as a bolus pump drive signal. The MEMS pump 1604 delivers the predetermined bolus volume to the patient 1608 in response to the bolus pump drive signal. In one embodiment, the bolus needle button 1616 triggers a switch in the path of button mechanism travel which starts the bolus injection when the bolus injection flow path is complete. In one example, the predetermined bolus volume is 2 units of insulin. In another embodiment, the patient 1608 selects a desired predetermined bolus volume using the control switch 1626 and the display 1628 before initiating the bolus injection. In this example, the basal and bolus drugs are the same drug, coming from the same fluid reservoir 1602 and going through the same flow path, but administered at different rates. The basal injection flows constantly at a very low rate. When a bolus injection is requested, the regulator 1622 changes the pump drive signal 1623 from the basal pump drive signal to a bolus delivery signal. When the bolus delivery is complete, the regulator 1622 changes the pump drive signal 1623 from the bolus pump drive signal to the basal delivery signal and basal injection resumes. In other embodiments, the basal injection flow path can include an orifice, check valve, or be sized so that the fluid does not flow forward or backward through the basal injection flow path during bolus injection.

The electronic on-body injector can optionally include a fill port (not shown) to fill or refill the fluid reservoir 1602. In one embodiment, the fluid reservoir 1602 can be pre-filled with a therapeutic agent when the on-body injector is delivered to the patient, so that the fill port is used for refilling the fluid reservoir 1602. In another embodiment, the fluid reservoir 1602 is empty when the electronic on-body injector is delivered to the patient, so that the fill port is used for initially filling the fluid reservoir 1602. In yet another embodiment, the fill port is omitted and the electronic on-body injector is a single use device with the fluid reservoir 1602 pre-filled with a therapeutic agent.

For one embodiment of an electronic on-body injector for a bolus injection for use with a patient 1608 to deliver a fluid through an injection device, the injection device has an injection port 1614 in fluid communication with a delivery tube 1606 with the injection port 1614 lying on an injection axis. The electronic on-body injector includes a fluid reservoir 1602 operable to hold the fluid; a MEMS pump 1604 in fluid communication with the fluid reservoir 1602; a bolus injection needle 1610 in fluid communication with the MEMS pump 1604, the bolus injection needle 1610 having a bolus injection needle tip aligned with the injection port, the bolus injection needle 1610 being slideably biased away from the injection port to define a gap 1612 between the bolus injection needle tip and the injection port; and a bolus needle button 1616 operably connected to the bolus injection needle 1610 to slide the bolus injection needle 1610 along the injection axis. the bolus needle button 1616 is operable to advance the bolus injection needle tip to close the gap 1612 and advance the bolus injection needle tip into the injection port to form a bolus injection flow path from the fluid reservoir 1602, through the MEMS pump 1604, through the bolus injection needle 1610, through the delivery tube 1606, and into the patient 1608. The bolus needle button 1616 is further operable to activate the MEMS pump 1604 to deliver a predetermined bolus volume to the patient 1608 through the bolus injection flow path in response to a bolus pump drive signal.

The electronic on-body injector for bolus injection can also include a battery 1620 having a DC power output 1621; a regulator 1622 operably connected to the battery 1620 to convert the DC power output 1621 to the bolus pump drive signal in response to a regulator control signal 1625; and a microcontroller 1624 operably connected to the regulator 1622 to provide the regulator control signal 1625. The MEMS pump 1604 is responsive to the bolus pump drive signal to control flow of the fluid from the MEMS pump 1604 through the bolus injection flow path.

For one embodiment of an electronic on-body injector for a basal injection for use with a patient 1608 to deliver a fluid through an injection device, the injection device has a delivery tube 1606. The electronic on-body injector includes a fluid reservoir 1602 operable to hold the fluid; and a MEMS pump 1604 in fluid communication with the fluid reservoir 1602 and the delivery tube 1606 to form a basal injection flow path from the fluid reservoir 1602, through the MEMS pump 1604, through the delivery tube 1606, and into the patient 1608. The MEMS pump 1604 is operable to deliver a basal injection to the patient 1608 through the basal injection flow path in response to a basal pump drive signal.

The electronic on-body injector for basal injection can also include a battery 1620 having a DC power output 1621; a regulator 1622 operably connected to the battery 1620 to convert the DC power output 1621 to the basal pump drive signal in response to a regulator control signal 1625; and a microcontroller 1624 operably connected to the regulator 1622 to provide the regulator control signal 1625. The MEMS pump 1604 is responsive to the basal pump drive signal to control flow of the fluid from the MEMS pump 1604 through the basal injection flow path. Exemplary batteries 1620 include non-rechargeable alkaline batteries rechargeable lithium-ion batteries, rechargeable lithium ion polymer batteries, and the like. In one example, the battery capacity is in the range of 200-500 mAh, In one example, the battery dimensions are 15×40×5 mm. Those skilled in the art will appreciate that the battery type, capacity, and size can be selected as desired for a particular application. Exemplary microcontrollers 1624 include the CC2541 (Bluetooth/microprocessor combination) from Texas Instruments, PSoC®4 (microcontroller) from Cypress Semiconductor Corporation, or the like. Those skilled in the art will appreciate that the microcontrollers can be selected as desired for a particular application.

Figure 32A:
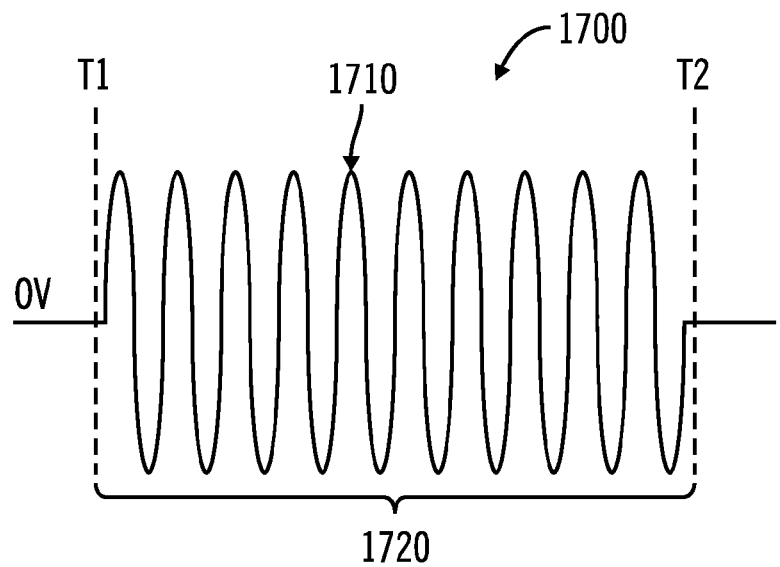
FIGS. 32A-32C are wave form diagrams of bolus, basal, and basal pump drive signals for an electronic injector made in accordance with the invention.
Figure 32B:
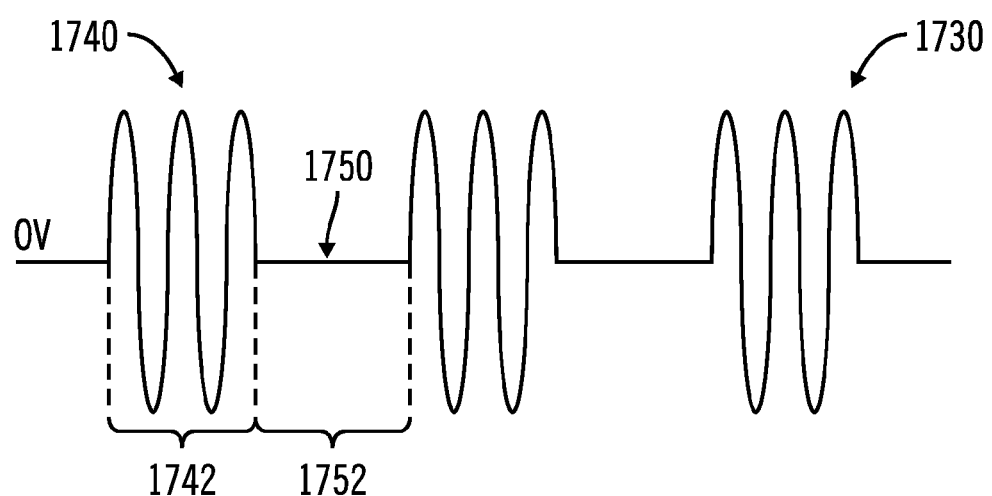
Figure 32C:
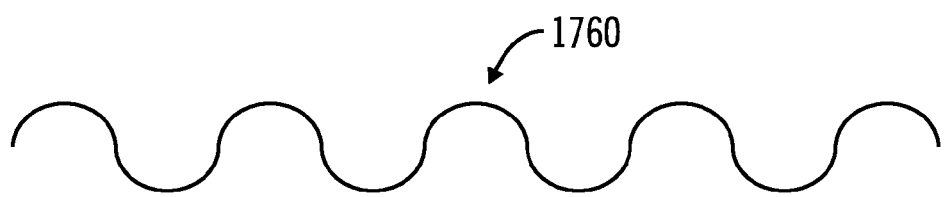

FIGS. 32A-32C are wave form diagrams of bolus, basal, and basal pump drive signals, respectively, for an electronic injector made in accordance with the invention. The frequency, amplitude, and duration of the AC portion of the pump drive signal determine the amount of fluid which is injected.

The bolus pump drive signal is selected to provide a predetermined bolus volume from the MEMS pump in response to a single bolus injection request from a patient. Referring to the example of FIG. 32A, the bolus pump drive signal 1700 includes an AC power signal 1710 for a predetermined duration 1720 between time T1 when the patient requests a bolus injection until the time T2 when the predetermined bolus volume has been delivered. The bolus pump drive signal 1700 has a value of 0 V DC before and after the AC power signal 1710. The MEMS pump moves the fluid when the AC power signal 1710 is active. In this example, the AC power signal 1710 is a sine wave. Those skilled in the art will appreciate that the pump drive signal can have any AC waveform as desired for a particular application. For example, the AC waveform can be a sine wave, a saw tooth wave, a square wave, or the like.

The basal pump drive signal is selected to provide a desired basal flow rate from the MEMS pump. Referring to the example of FIG. 32B, the basal pump drive signal 1730 includes a series of AC power signals 1740 of AC power duration 1742 alternating with zero volt power signals 1750 of zero volt power duration 1752. The time of AC power duration 1742 and/or 0 V power duration 1752 can be selected to provide the desired basal flow rate. The MEMS pump moves the fluid when each of the AC power signals 1740 is active. In this example, the AC power signal 1740 is a sine wave. Those skilled in the art will appreciate that the pump drive signal can have any AC waveform as desired for a particular application. For example, the AC waveform can be a sine wave, a saw tooth wave, a square wave, or the like.

FIG. 32C is an example of a continuous basal pump drive signal, which provides a continuous AC waveform. The basal pump drive signal 1760 has a frequency and/or amplitude which is substantially less than the AC power signal of FIG. 32A or FIG. 32B, so that the basal pump drive signal 1760 is continuously applied to the MEMS pump to provide a desired basal flow rate from the MEMS pump. In this example of FIG. 32C, the basal pump drive signal 1760 is a sine wave. Those skilled in the art will appreciate that the basal pump drive signal can have any AC waveform as desired for a particular application. For example, the basal pump drive signal can be a sine wave, a saw tooth wave, a square wave, or the like.

Figure 33A:
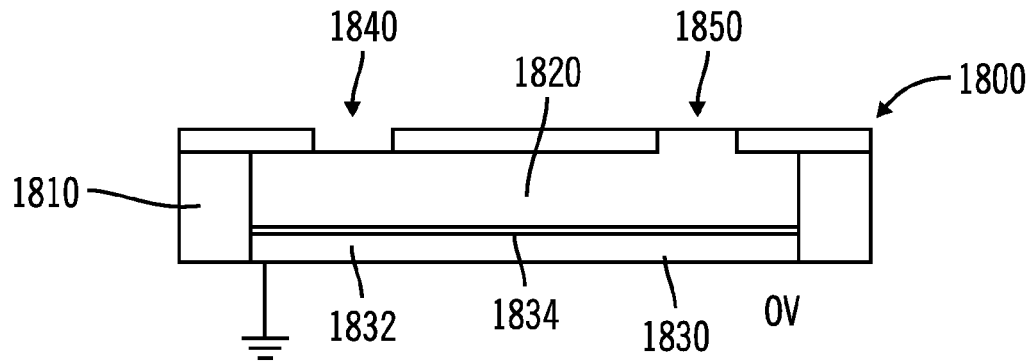
FIGS. 33A-33C are schematic diagrams of a piezoelectric MEMS pump for use in an electronic injector made in accordance with the invention.
Figure 33B:
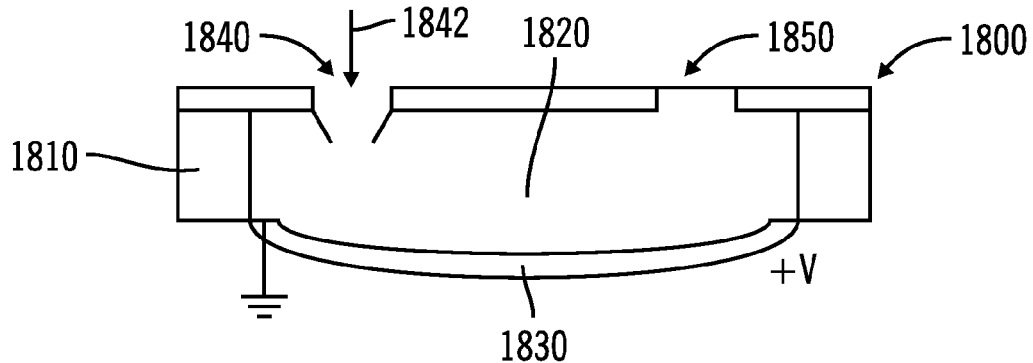
Figure 33C:
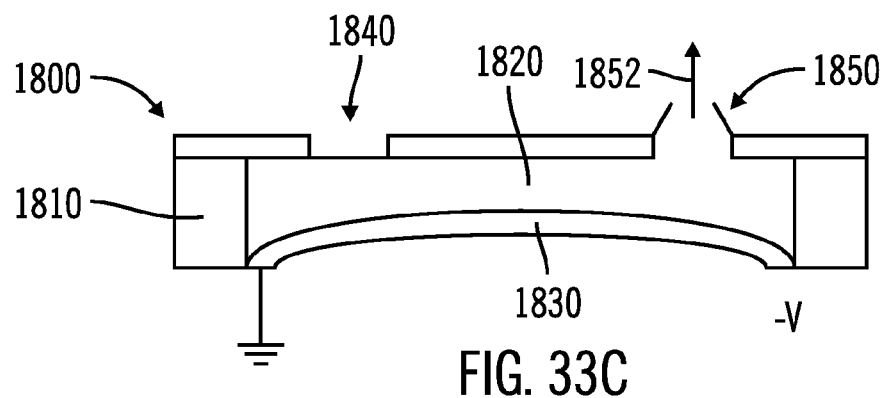

FIGS. 33A-33C, in which like elements share like reference numbers, are schematic diagrams of a piezoelectric MEMS pump for use in an electronic injector made in accordance with the invention. FIG. 33A illustrates the MEMS pump at rest, FIG. 33B illustrates the MEMS pump during fluid intake, and FIG. 33C illustrates the MEMS pump during fluid output.

Referring to FIG. 33A illustrating the MEMS pump at rest, the piezoelectric MEMS pump 1800 includes a case 1810 defining a working chamber 1820, the working chamber 1820 having a piezoelectric wall 1830 responsive to a first pump drive signal voltage and a second pump drive signal voltage; a one way inlet valve 1840 operable to permit flow of the fluid into the working chamber 1820 and to block reverse flow of the fluid from the working chamber 1820; and a one way outlet valve 1850 operable to permit flow of the fluid from the working chamber 1820 and to block reverse flow of the fluid into the working chamber 1820. The one way inlet valve 1840 is in fluid communication with the fluid reservoir (not shown). When the piezoelectric MEMS pump 1800 is used for bolus injection, the one way outlet valve 1850 is in fluid communication with the bolus injection needle (not shown). When the piezoelectric MEMS pump 1800 is used for basal injection, the one way outlet valve 1850 is in fluid communication with the delivery tube (not shown). In one embodiment, the piezoelectric wall 1830 includes a piezoelectric disk 1832 with a membrane 1834 sealing the working chamber 1820. The working chamber 1820 can be etched directly out of the silicon base material. The flexible membrane 1834 can be a thin layer of silicon or silicon dioxide. The piezoelectric disk 1832 can be attached to the flexible membrane 1834.

Referring to FIG. 33B illustrating the MEMS pump during fluid intake, the piezoelectric wall 1830 flexes outward to increase volume of the working chamber 1820 in response to the first pump drive signal voltage (+V to ground across the piezoelectric wall 1830) to draw the fluid through the one way inlet valve to the working chamber 1820 as indicated by the arrow 1842.

Referring to FIG. 33C illustrating the MEMS pump during fluid output, the piezoelectric wall 1830 flexes inward to decrease the volume of the working chamber 1820 in response to the second pump drive signal voltage (−V to ground across the piezoelectric wall 1830) to force the fluid from the working chamber 1820 through the one way outlet valve 1850 as indicated by the arrow 1852.

Alternately applying the first pump drive signal voltage and the second pump drive signal voltage causes the piezoelectric wall 1830 to oscillate, pumping fluid through the piezoelectric MEMS pump 1800. In one embodiment, the first pump drive signal voltage and the second pump drive signal voltage are applied as a pump drive signal as a square wave. The piezoelectric MEMS pump 1800 can be fabricated using standard semiconductor techniques, resulting in a pump of reduced size and improved accuracy compared to standard mechanical pumps. In one example, the piezoelectric MEMS pump 1800 can deliver flow rates up to 3 milliliters per minute, which is the equivalent of 300 units of insulin per minute or 5 units of insulin per second. Those skilled in the art will appreciate that the MEMS pump is not limited to a piezoelectric MEMS pump, but can be a bimetallic pump, an electrostatic pump, a thermopneumatic pump, an electromagnetic pump, a phase change pump, or the like, as desired for a particular application.

Figure 34A:
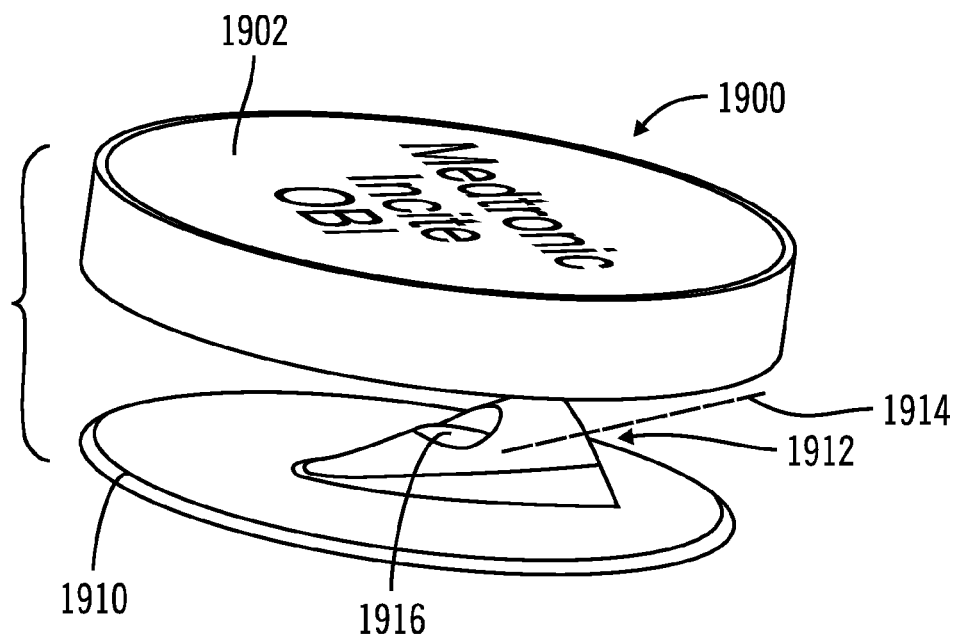
FIGS. 34A-34C are an exploded perspective view, a partial perspective view, and a partial perspective view of an injection device and electronic on-body injector made in accordance with the invention.
Figure 34B:
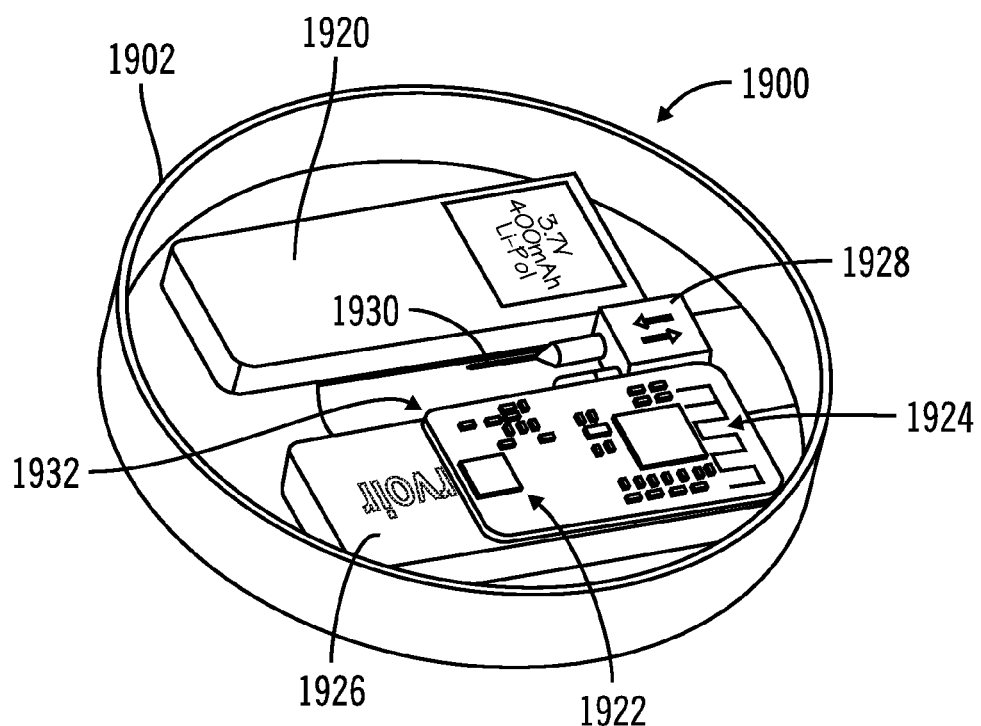
Figure 34C:
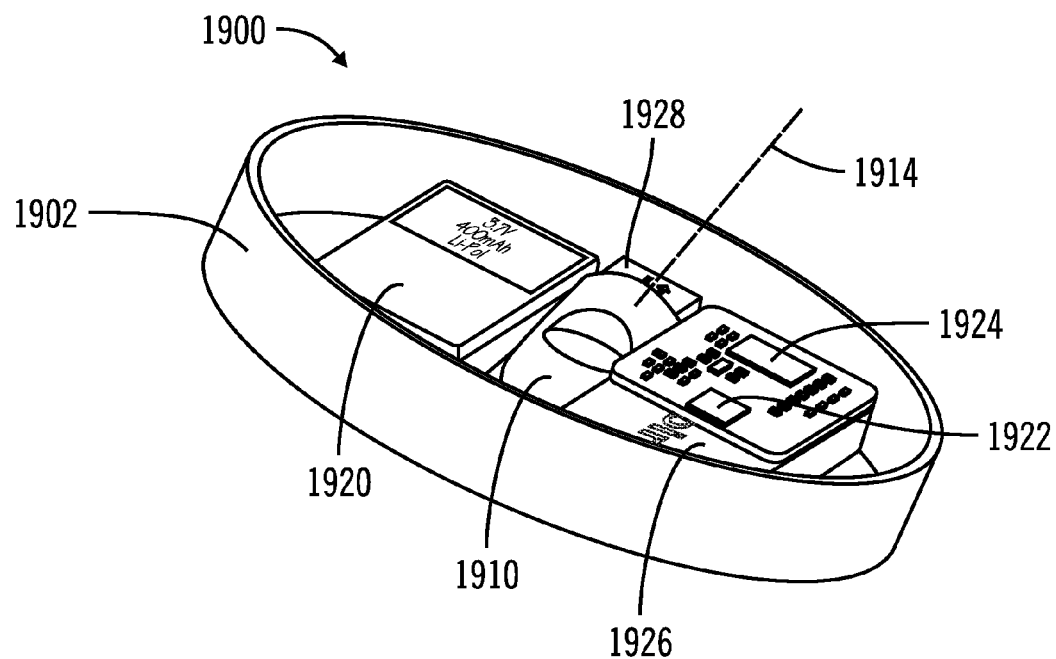

FIGS. 34A-34C, in which like elements share like reference numbers, are an exploded perspective view, a partial perspective view, and a partial perspective view of an injection device and electronic on-body injector made in accordance with the invention. In this embodiment, the electronic on-body injector is the electronic injector.

Referring to FIG. 34A, the electronic on-body injector 1900 is illustrated separated from the injection device 1910. The electronic on-body injector 1900 has a housing 1902 to contain the internal components of the electronic on-body injector 1900. The injection device 1910 has an injection port 1912 lying on an injection axis 1914 as illustrated by the dashed line. The injection device 1910 in this example also has an introducer port 1916.

Referring to FIG. 34B, which illustrates the electronic on-body injector 1900 with the top of the housing 1902 removed, the interior of the housing 1902 of the electronic on-body injector 1900 encloses the battery 1920, the regulator 1922, the microcontroller 1924, the fluid reservoir 1926, and the MEMS pump 1928. The bolus injection needle 1930 is partially enclosed within the housing 1902 with the bolus injection needle tip 1932 extending from the housing 1902 to access the injection device. Various controls and indicators (not shown), such as the bolus needle button, control switches, displays, and the like, can extend through and/or be positioned upon the housing 1902. FIG. 34C illustrates the electronic on-body injector 1900 in place on the injection device 1910. The bolus injection needle (not shown) is aligned with the injection axis 1914 of the injection device 1910.

Figure 35:
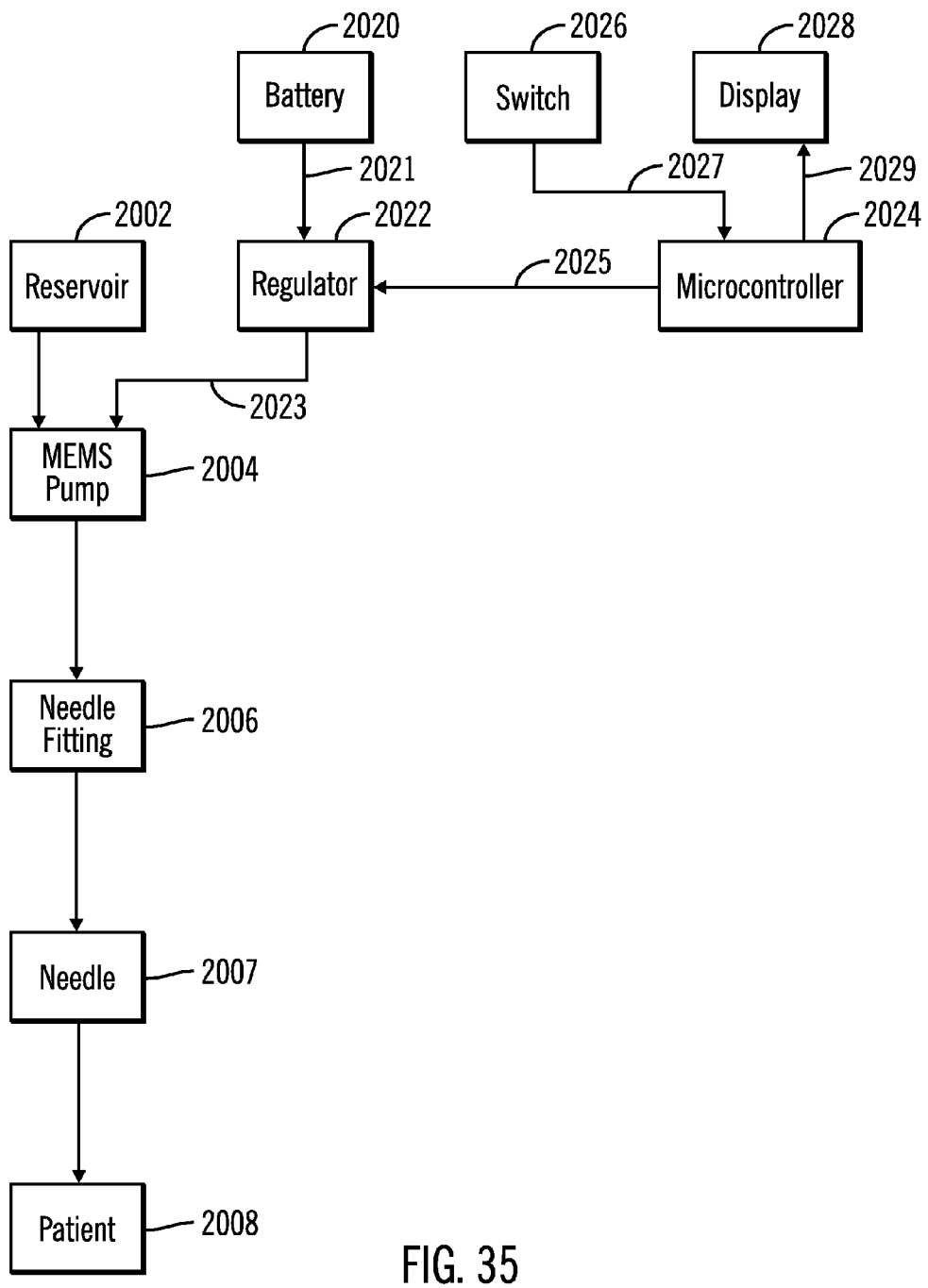
FIG. 35 is a block diagram of one embodiment of an electronic injector made in accordance with the invention.

FIG. 35 is a block diagram of one embodiment of an electronic injector made in accordance with the invention. FIG. 35 illustrates the flow paths through and electrical signals for the electronic injector, which can be used for injection of a therapeutic agent.

The basal injection flow path includes a fluid reservoir 2002, a MEMS pump 2004, a needle fitting 2006, and an injection needle 2007 supplying the patient 2008. In one embodiment, the injection needle 2007 is detachable from the needle fitting 2006 so that the injection needle 2007 can be replaced at a desired frequency, e.g., after each injection. In another embodiment, the injection needle 2007 is permanently attached to the needle fitting 2006. In yet another embodiment, no injection needle is used, but the tip of the electronic injector is adapted for use as a needleless pen injector as described in conjunction with FIGS. 11 & 12 above.

Referring to FIG. 35, the electronic portion of the electronic injector includes a battery 2020, a regulator 2022, and a microcontroller 2024. The battery 2020 has a DC power output 2021 which is provided to the regulator 2022. The battery 2020 is also operably connected (not shown) to provide power to the microcontroller 2024. The regulator 2022 is operably connected to the battery 2020 to convert the DC power output 2021 to a pump drive signal 2023 in response to a regulator control signal 2025 from the microcontroller 2024. The regulator 2022 provides the pump drive signal 2023 to the MEMS pump 2004. The MEMS pump 2004 is responsive to the pump drive signal 2023 to control flow of the fluid from the fluid reservoir 2002, through the MEMS pump 2004, through the needle fitting 2006, through the needle 2007, and into the patient 2008. In one embodiment, the MEMS pump 2004 is a piezoelectric MEMS pump as described in conjunction with FIGS. 33A-33C above. In other embodiments, the MEMS pump 2004 can be a bimetallic pump, an electrostatic pump, a thermopneumatic pump, an electromagnetic pump, a phase change pump, or the like, as desired for a particular application.

Referring to FIG. 35, the microcontroller 2024 controls the electronic injector. The microcontroller 2024 provides the regulator control signal 2025 to the regulator 2022, controlling the pump drive signal 2023. The microcontroller 2024 can be responsive to a control switch signal 2027 from a control switch 2026 and/or can provide a display signal 2029 to a display 2028. The control switch 2026 and the display 2028 can be used to provide input and output, respectively, to the electronic injector. For example, the display 2028 can be used to display injection options, such as the bolus injection volume, and control switch 2026 can be used to select one of the injection options. The microcontroller 2024 can also include or be associated with memory to store data and/or instructions. The microcontroller 2024 can also be operably connected to one or more sensors to monitor the patient 2008 and/or a wireless interface to communicate with one or more external sensors monitoring the patient 2008 or external communication and/or control systems, such as the internet, a continuous glucose monitoring system, a mobile device, or the like. Exemplary uses for a wireless interface providing communication between the electronic injector and an external system/device include calculating/setting dosages, tracking injection times and volumes, and/or sending reminders to a paired device (computer, phone, tablet, mobile device, or the like).

For bolus injection, the fluid reservoir 2002 of the on-body injector provides the therapeutic agent to the patient 2008 through the injection flow path (the fluid reservoir 2002, MEMS pump 2004, needle fitting 2006, and injection needle 2007). In one embodiment, the patient 2008 initiates a bolus injection by pressing the control switch 2026, which provides the control switch signal 2027 to the microcontroller 2024, which provides the regulator control signal 2025 to the regulator 2022. In this case, the regulator control signal 2025 is a bolus regulator control signal and the regulator 2022 generates the pump drive signal 2023 as a bolus pump drive signal. The MEMS pump 2004 delivers the desired bolus injection to the patient 2008 in response to the bolus pump drive signal. In another embodiment, the patient 2008 selects a predetermined bolus volume using the control switch 2026 and the display 2028 before initiating the bolus injection. In one example, the predetermined bolus volume is 2 units of insulin.

The electronic injector can optionally include a fill port (not shown) to fill or refill the fluid reservoir 2002. In one embodiment, the fluid reservoir 2002 can be pre-filled with a therapeutic agent when the on-body injector is delivered to the patient, so that the fill port is used for refilling the fluid reservoir 2002. In another embodiment, the fluid reservoir 2002 is empty when the electronic injector is delivered to the patient, so that the fill port is used for initially filling the fluid reservoir 2002. In yet another embodiment, the fill port is omitted and the electronic injector is a single use device with the fluid reservoir 2002 pre-filled with a therapeutic agent.

For one embodiment of an electronic injector for use with a patient 2008 to deliver a fluid, the electronic injector includes a fluid reservoir 2002 operable to hold the fluid; a MEMS pump 2004 in fluid communication with the fluid reservoir 2002; a needle fitting 2006 adapted to receive an injection needle, the needle fitting 2006 being in fluid communication with the MEMS pump 2004; a battery 2020 having a DC power output 2021; a regulator 2022 operably connected to the battery 2020 to convert the DC power output 2021 to a pump drive signal 2023 in response to a regulator control signal 2025; a microcontroller 2024 operably connected to the regulator 2022 to provide the regulator control signal 2025; and a housing to enclose the battery 2020, the regulator 2022, the microcontroller 2024, the fluid reservoir 2002, and the MEMS pump 2004. The MEMS pump 2004 is responsive to the pump drive signal 2023 to control flow of the fluid from the fluid reservoir 2002, through the MEMS pump 2004, through the injection needle 2007, and into the patient 2008.

FIGS. 36A-36D, in which like elements share like reference numbers, are a perspective view, a top view, a side view, and a partial perspective view of an electronic injector made in accordance with the invention. In this example, the electronic injector has a pen form factor, which in this example has a length less than or equal to 125 mm, a width less than or equal to 20 mm, and a height less than or equal to 9 mm.

Figure 36A:
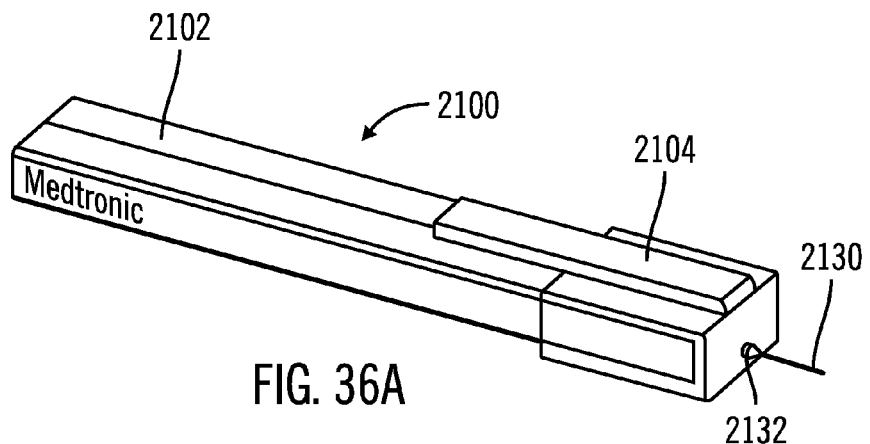
FIGS. 36A-36D are a perspective view, a top view, a side view, and a partial perspective view of an electronic injector made in accordance with the invention.
Figure 36B:
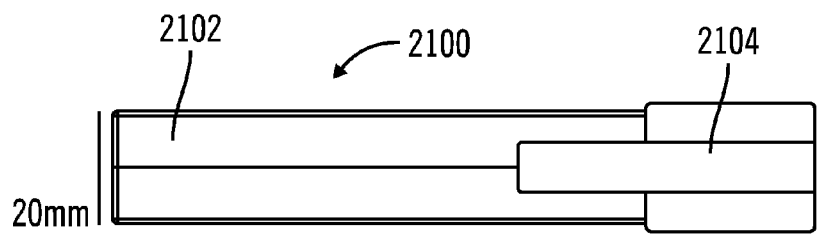
Figure 36C:
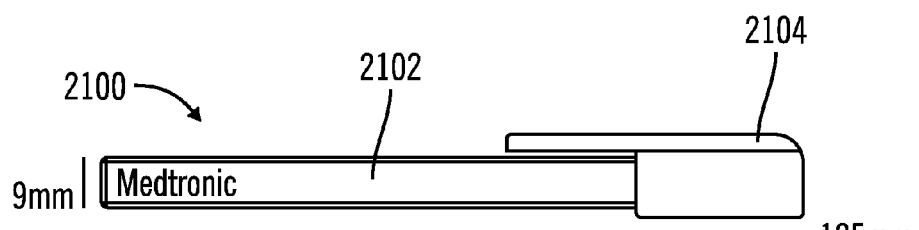

Referring to FIGS. 36A-36C, the electronic injector 2100 has a housing 2102 to contain the internal components of the electronic injector 2100. The injection needle 2130 is attached to the electronic injector 2100 at the needle fitting 2132. In this example, the electronic injector 2100 also includes a cap 2104 removeable from the housing 2102. In one embodiment, the housing 2102 can include a control switch (not shown) which can be used to initiate an injection.

Figure 36D:
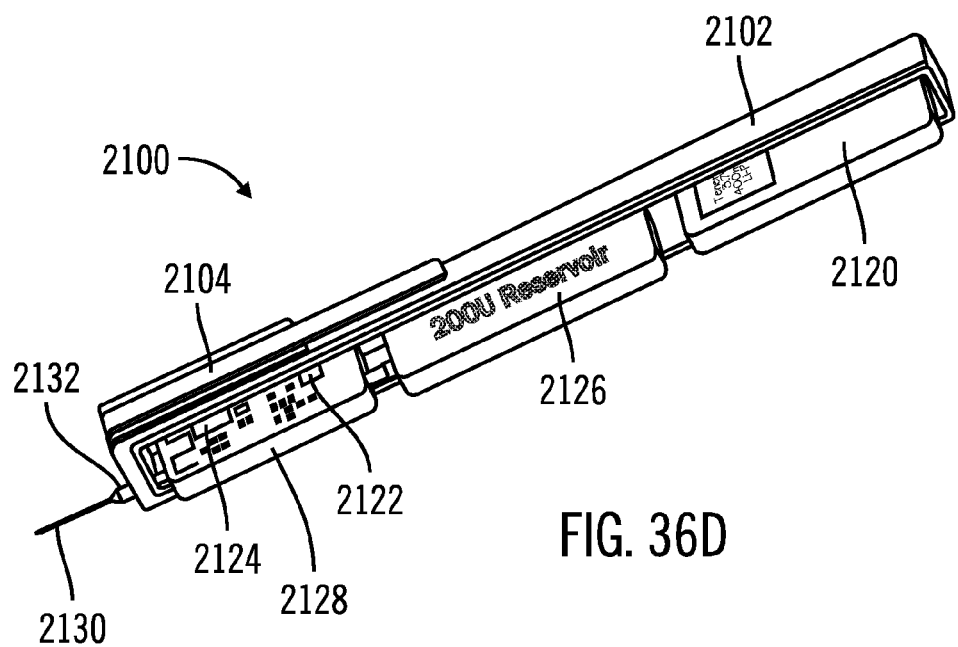

Referring to FIG. 36D, which illustrates the electronic injector 2100 with a portion of the housing 2102 removed, the interior of the housing 2102 of the electronic injector 2100 encloses the battery 2120, the regulator 2122, the microcontroller 2124, the fluid reservoir 2126, and the MEMS pump 2128. Various controls and indicators (not shown), such as control switches, displays, and the like, can extend through and/or be positioned upon the housing 2102.

FIGS. 37A-37E, in which like elements share like reference numbers, are a perspective view, a top view, a side view, an exploded perspective view, and a partial top view of an electronic injector made in accordance with the invention. In this example, the electronic injector has a card form factor, which in this example has a length less than or equal to 85 mm, a width less than or equal to 55 mm, and a height less than or equal to 8 mm.

Figure 37A:
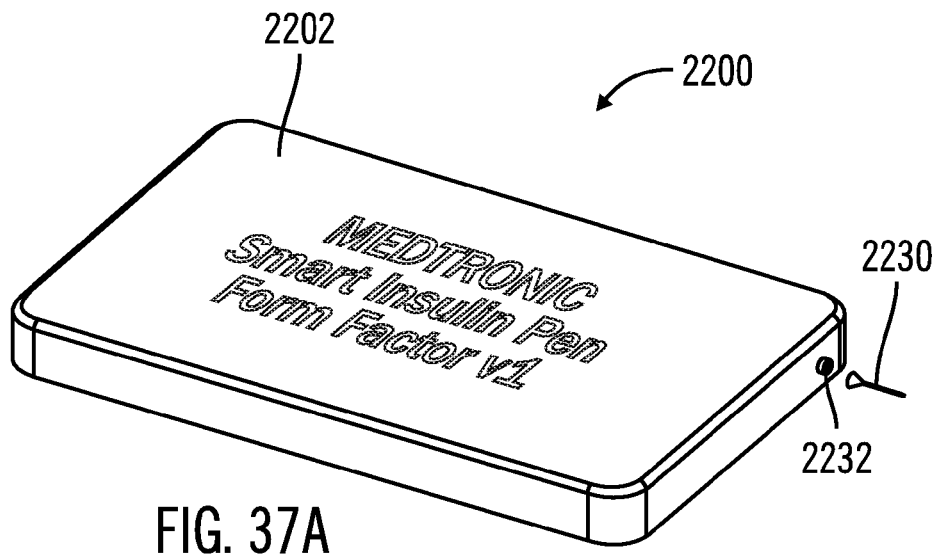
FIGS. 37A-37E are a perspective view, a top view, a side view, an exploded perspective view, and a partial top view of an electronic injector made in accordance with the invention.
Figure 37B:
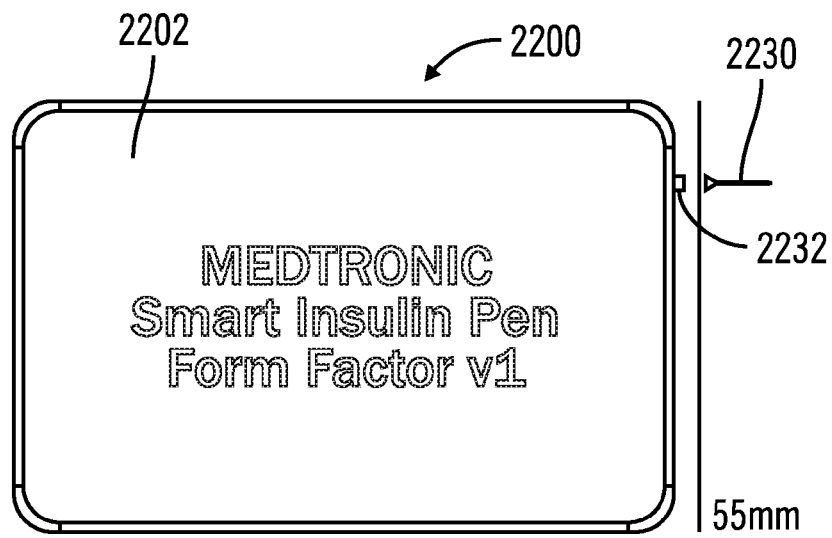
Figure 37C:
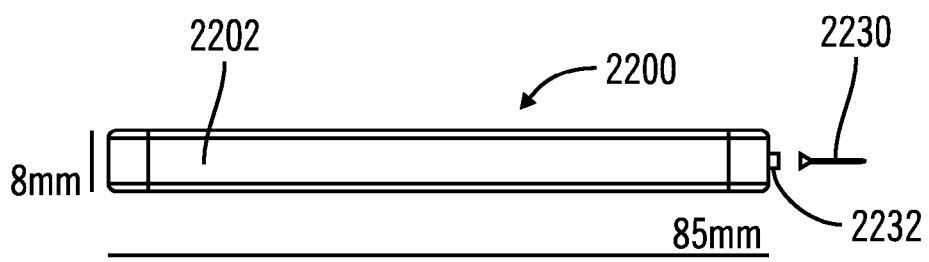

Referring to FIGS. 37A-37C, the electronic injector 2200 has a housing 2202 to contain the internal components of the electronic injector 2200. The injection needle 2230 can be attached to the electronic injector 2200 at the needle fitting 2232.

Figure 37D:
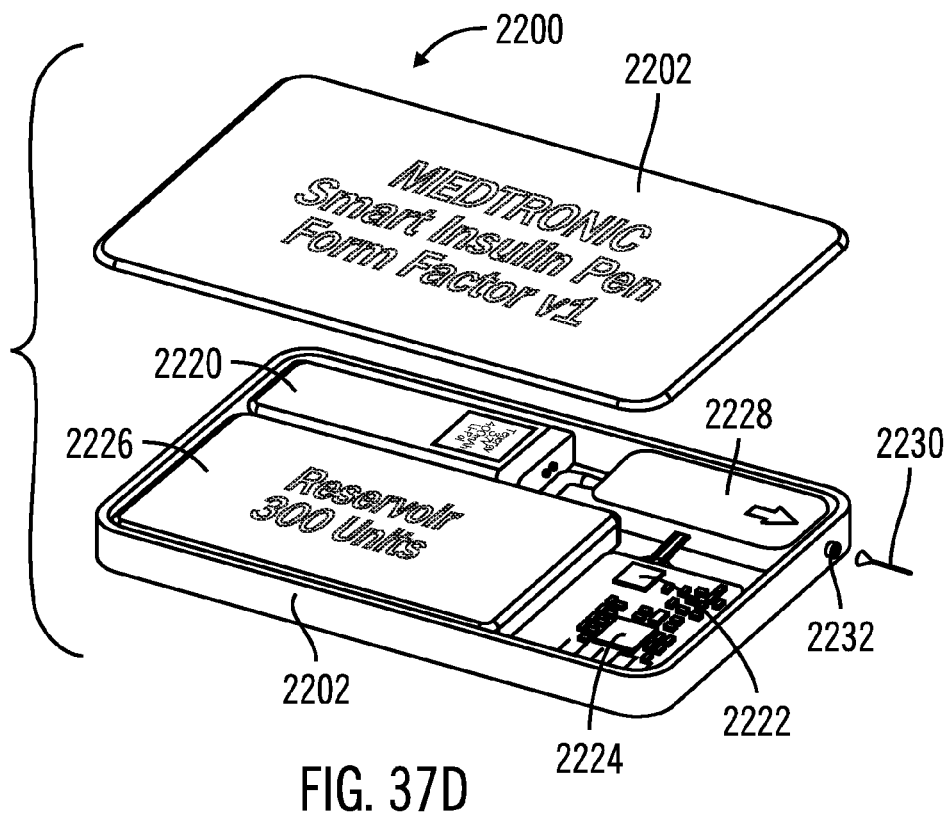
Figure 37E:
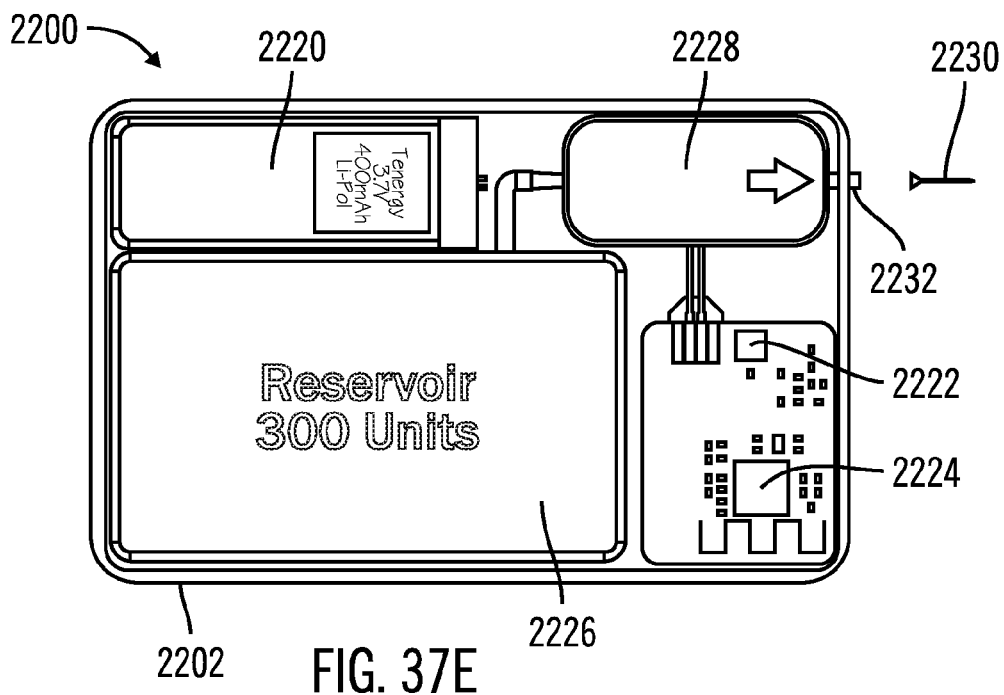

Referring to FIGS. 37D & 37E, which illustrate the electronic injector 2200 with a top portion of the housing 2202 removed, the interior of the housing 2202 of the electronic injector 2200 encloses the battery 2220, the regulator 2222, the microcontroller 2224, the fluid reservoir 2226, and the MEMS pump 2228. Various controls and indicators (not shown), such as control switches, displays, and the like, can extend through and/or be positioned upon the housing 2202.

Figure 38:
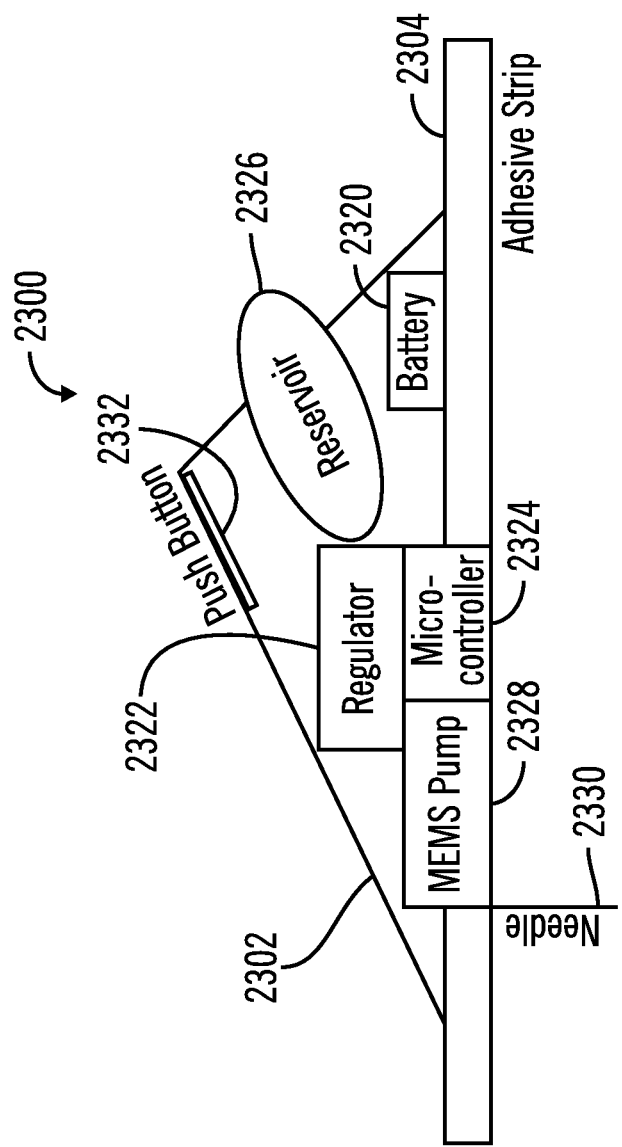
FIG. 38 is a schematic cross section view of an electronic injector made in accordance with the invention.

FIG. 38 is a schematic cross section view of an electronic injector made in accordance with the invention. The electronic injector includes an adhesive patch operable to secure the housing to the patient.

The electronic injector 2300 has a housing 2302 to contain the internal components of the electronic injector 2300. The injection needle 2330 protrudes through the adhesive strip 2304, which forms the bottom of the housing 2302 for adhesively attaching the electronic injector 2300 to the patient. The interior of the housing 2302 of the electronic injector 2300 encloses the battery 2320, the regulator 2322, the microcontroller 2324, the fluid reservoir 2326, and the MEMS pump 2328. Various controls and indicators (not shown), such as control switches, displays, and the like, can extend through and/or be positioned upon the housing 2302. In one embodiment, the electronic injector 2300 includes a push button 2332 which can be used to initiate delivery of a therapeutic agent to the patient.

The electronic injector as described in conjunction with FIGS. 31-38 above can be extended to include additional features for convenience, ease-of-use, and safety.

The electronic injector can include wireless functionality, allowing communication with local or remote communication devices. Examples of wireless connections include Bluetooth, Bluetooth Low Energy, Near Field Communication or 802.11 Wi-Fi, and the like. This wireless communication can be used to pull injection data from the electronic injector and to interface with the electronic injector, including inputting data to calculate injection dosages, directly inputting injection dosages, setting timers, reminders, and safety lockouts. In one embodiment, the electronic injector can be paired with an on-body continuous glucose monitor to calculate the desired bolus injection volume for the electronic injector and avoid manual entry. In this embodiment, both the Continuous Glucose Monitor (CGM) and the injector can be paired with a wireless device running a control application. The wireless device can read in the current glucose level of the patient from the CGM and the patient can manually enter their weight/insulin resistance information (which can be saved for future use and updated as needed) along with their intended sugar intake. the mobile device control application can then calculate the injection volume and send that information back to the electronic injector. In this embodiment, neither the electronic injector nor the CGM has the computational capability to do this calculation. In another embodiment, the CGM can connect directly to the electronic injector. The patient can perform an initial step of loading in their weight and treatment resistance information. During normal use, the patient would only enter the amount of food they plan to consume. The electronic injector can then calculate the correct dosage for the patient. In another embodiment, the electronic injector can wirelessly connect to the CGM to read the patient's current glucose levels, then can take direct patient input on incoming sugars. The electronic injector can then perform the dosage calculation with no other wireless device involved. In another embodiment, the electronic injector can be paired with a communication device (computer, phone, tablet, etc.) which tracks usage data obtained by the electronic injector. Exemplary data include tracking of injection times and injection amounts, which can be used to establish trends and/or to verify that proper injections occurred at proper times. Such tracking could be particularl useful in caring for the young and the elderly. In yet another embodiment, the electronic injector can obtain and/or provide data to remote medical databases, such as the Medtronic CareLink Network, to provide an easy and quick interface between the patient and physician in an effort to continuously manage the patient's treatment. This would be particularly useful for new patients that need to make frequent adjustments to their dosage until the patient and doctor determine the correct dosages to use.

The electronic injector can also include safety features. In one embodiment, the electronic injector can remind the patient when it is the proper time for a basal injection by use of a vibration, auditory, and/or visual signal at a preset or predetermined time. The electronic injector can also verify that injections occur at the proper injection time with the proper injection amount, and provide the data to remote medical databases or control applications over a paired communication device. In another embodiment, the electronic injector can provide a warning or injection lockout when a second injection is attempted within a certain time period, preventing accidental double injections. In yet another embodiment when the therapeutic agent is provided in a replaceable reservoir, the electronic injector can detect the type of replaceable reservoir and/or recognize the type of insulin or other therapeutic agent being used, and adjust the operation of the electronic injector automatically. Each reservoir can have a unique ID tag, which can take the form of an RFID tag, EEPROM, a variable resistance, a small optical tag, or the like, that the electronic injector can scan to identify the specific reservoir type, contents, and/or expiration date.

The electronic injector can also include device monitoring features. In one embodiment, the electronic injector can verify the flow rate of the therapeutic agent using a MEMS flow meter to assure that it is correct. When the flow rate is too high, the electronic injector can stop the injection to avoid an excessive delivery of the therapeutic agent. When the flow rate is too low, the electronic injector can stop the pump to avoid build up of excessive delivery pressure due to an obstruction in the flowpath, such as a kink in the tubing. In either situation, the electronic injector can send a warning to the patient via a vibration, auditory signal, and/or visual signal through either the electronic injector or paired mobile device indicating that the injection has stopped. In another embodiment, the electronic injector can have a temperature sensor that monitors the temperature of the therapeutic agent within the reservoir. When the therapeutic agent temperature rises above or falls below recommended thresholds, the electronic injector can warn the patient via a vibration, auditory signal, and/or visual signal that the therapeutic agent may no longer be safe to use. In another embodiment, the electronic injector can provide a low battery warning to warn the patient that the electronic injector may not be available for service. This warning can be a vibration, auditory signal, and/or visual signal. This warning can also pop up as a warning, such as a vibration, auditory signal, and/or visual signal, on a wirelessly connected mobile device. In yet another embodiment, the electronic injector can check the identity and/or the expiration date of the therapeutic agent when the therapeutic agent is provided in a replaceable reservoir. This information can be included in the unique ID tag described above.

The electronic injector can also include green technology features. In one embodiment, the electronic injector can harvest energy to recharge or replace the battery. The electronic injector can turn mechanical motion (button press, body motions) into electrical energy through a piezo energy harvesting module. In another embodiment, the electronic injector can use rechargeable batteries that can be recharged via an AC wall adapter, or a USB, mini USB or micro USB connector.

The electronic injector can also include therapeutic agent flexibility features. The electronic injector can work with existing therapeutic agents and new therapeutic agent coming onto the market. Along with insulin for diabetes treatment, the electronic injector can work with glucagon-like peptide-1 (GLP-1) or Amylin pancreatic hormone. The electronic injector can also be used with other therapeutic agents such as injectable pain medication, steroids, Botox, or the like. In one embodiment, the electronic injector can adapt operation to provide a maximum flow rate and/or lockout timer through internal control valves and utilizing a clock timer within the electronic injector to prevent abuse of the therapeutic agent. In one embodiment, the electronic injector can include dual reservoirs so that one electronic injector can provide different therapeutic agents to a patient requiring more than one type of therapeutic agent. In one example, one reservoir can house fast acting bolus insulin, e.g., Novolog, and the other reservoir can house slow acting basal insulin, e.g., Lantix.

The electronic injector can include convenience features to encourage the patient to use the device. In one embodiment, the electronic injector would be disposable with all the parts being prepackaged (including the therapeutic agent in the reservoir) and would be tossed away as soon as the therapeutic agent is used up or expires. In another embodiment, the electronic injector would be durable with a replaceable cartridge containing just the reservoir and MEMS micropump, which would snap into place and would require only an electrical connection to the durable parts of the pump. In this embodiment, the entire flow path (reservoir, MEMS pump, and injection needle port) for the therapeutic agent can be contained within the disposable cartridge, so that only an external electrical signal from the durable portion of the electronic injector is required to control the pump. In yet another embodiment, the electronic injector would be durable and only a replaceable cartridge including the therapeutic agent would be replaced. In this embodiment, the cartridge can make a mechanical connection to create the fluid flow path from the reservoir to the MEMS pump.

It is important to note that FIGS. 1-38 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. An on-body injector for use with a patient with an injection device having an injection port in fluid communication with a delivery tube, the injection port lying on an injection axis, the on-body injector comprising:
   a bolus reservoir;
   a bolus injection needle in fluid communication with the bolus reservoir; and
   a button operably connected to the bolus injection needle to slide the bolus injection needle along the injection axis;
   wherein the button is operable to advance the bolus injection needle to form an injection flow path from the bolus reservoir, through the bolus injection needle, through the delivery tube, and into the patient;
   wherein the button is further operable to advance a plunger through the bolus reservoir to deliver a predetermined bolus volume to the patient through the injection flow path; and
   wherein the plunger blocks the injection flow path when the plunger is at a final position in the bolus reservoir when the predetermined bolus volume has been delivered.

2. The on-body injector of claim 1, wherein the predetermined bolus volume is 2 units of insulin.

3. An on-body injector for use with a patient with an injection device having an injection port in fluid communication with a delivery tube, the injection port lying on an injection axis, the on-body injector comprising:
   a bolus reservoir;
   a bolus injection needle in fluid communication with the bolus reservoir; and
   a button operably connected to the bolus injection needle to slide the bolus injection needle along the injection axis;
   wherein the button is operable to advance the bolus injection needle to form an injection flow path from the bolus reservoir, through the bolus injection needle, through the delivery tube, and into the patient;
   wherein the button is further operable to advance a plunger through the bolus reservoir to deliver a predetermined bolus volume to the patient through the injection flow path; and
   the on-body injector further including a pressurized reservoir in fluid communication with the bolus reservoir.

4. The on-body injector of claim 3, wherein the injection device has an introducer port in fluid communication with the delivery tube, the pressurized reservoir being in fluid communication with the delivery tube through a flow restrictor.

5. The on-body injector of claim 4, wherein the flow restrictor is tubing having a length and interior diameter selected to provide a desired pressure drop.

6. The on-body injector of claim 4, wherein the flow restrictor is selected to provide a basal flow rate selected from the group consisting of 20 units of insulin per 24 hours, 30 units of insulin per 24 hours, and 40 units of insulin per 24 hours.

7. The on-body injector of claim 3, further comprising a fill port in fluid communication with the pressurized reservoir.

8. The on-body injector of claim 3, further comprising a housing defining an interior track, wherein the pressurized reservoir is a spring coil operable to at least partially uncoil within the interior track when the pressurized reservoir is at least partially filled with a therapeutic agent.

9. An on-body injector for use with a patient with an injection device having an injection port in fluid communication with a delivery tube, the injection port lying on an injection axis, the on-body injector comprising:
- a bolus reservoir;
- a bolus injection needle in fluid communication with the bolus reservoir; and
- a button operably connected to the bolus injection needle to slide the bolus injection needle along the injection axis;
- wherein the button is operable to advance the bolus injection needle to form an injection flow path from the bolus reservoir, through the bolus injection needle, through the delivery tube, and into the patient;
- wherein the button is further operable to advance a plunger through the bolus reservoir to deliver a predetermined bolus volume to the patient through the injection flow path; and
- the on-body injector further including a spring operable to slideably bias the bolus injection needle away from the injection port.

10. An on-body injector for use with a patient with an injection device having an injection port in fluid communication with a delivery tube, the injection port lying on an injection axis, the on-body injector comprising:
- a bolus reservoir;
- a bolus injection needle in fluid communication with the bolus reservoir; and
- a button operably connected to the bolus injection needle to slide the bolus injection needle along the injection axis;
- wherein the button is operable to advance the bolus injection needle to form an injection flow path from the bolus reservoir, through the bolus injection needle, through the delivery tube, and into the patient;
- wherein the button is further operable to advance a plunger through the bolus reservoir to deliver a predetermined bolus volume to the patient through the injection flow path; and
- the on-body injector further including a lock operable to secure the on-body injector to the injector device.

11. An on-body injector for use with a patient with an injection device having an introducer port in fluid communication with a delivery tube, the on-body injector comprising:
- a pressurized reservoir;
- a flow restrictor disposed between the pressurized reservoir and the delivery tube, wherein a basal flow path is formed from the pressurized reservoir, through the flow restrictor, through the introducer port, through the delivery tube, and into the patient;
- a bolus reservoir;
- a bolus injection needle in fluid communication with the bolus reservoir; and
- a button operably connected to the bolus injection needle to slide the bolus injection needle along the injection axis;
- wherein the button is operable to advance the bolus injection needle to form an injection flow path from the bolus reservoir, through the bolus injection needle, through the delivery tube, and into the patient;
- wherein the button is further operable to advance a plunger through the bolus reservoir to deliver a predetermined bolus volume to the patient through the injection flow path.

12. The on-body injector of claim 11, wherein the flow restrictor is tubing having a length and interior diameter selected to provide a desired pressure drop.

13. The on-body injector of claim 11, wherein the flow restrictor is selected to provide a basal flow rate selected from the group consisting of 20 units of insulin per 24 hours, 30 units of insulin per 24 hours, and 40 units of insulin per 24 hours.

14. The on-body injector of claim 11, further comprising a fill port in fluid communication with the pressurized reservoir.

15. The on-body injector of claim 11, further comprising a housing defining an interior track, wherein the pressurized reservoir is a spring coil operable to at least partially uncoil within the interior track when the pressurized reservoir is at least partially filled with a therapeutic agent.

16. The on-body injector of claim 11, wherein the plunger blocks the injection flow path when the plunger is at a final position in the bolus reservoir when the predetermined bolus volume has been delivered.

17. The on-body injector of claim 11, further comprising a spring operable to slideably bias the bolus injection needle away from the injection port.

18. The on-body injector of claim 11, further comprising a lock operable to secure the on-body injector to the injection device.

* * * * *